United States Patent
Sundvor et al.

(10) Patent No.: US 9,939,432 B2
(45) Date of Patent: Apr. 10, 2018

(54) SYSTEM AND METHOD FOR DETECTION OF TARGET SUBSTANCES

(71) Applicant: 6SensorLabs, Inc., San Francisco, CA (US)

(72) Inventors: Scott Sundvor, San Francisco, CA (US); Steven Portela, San Francisco, CA (US); Jonathan Ward, San Francisco, CA (US); John Walton, Cambridge, MA (US); Jonathan William Kiel, Ardmore, PA (US); Jeffrey Mekler, Cambridge, MA (US); Shireen Yates, San Francisco, CA (US); Jacob Mooney, Westford, MA (US)

(73) Assignee: Nima Labs, Inc., San Francisco, CA (US)

( * ) Notice: Subject to any disclaimer, the term of this patent is extended or adjusted under 35 U.S.C. 154(b) by 600 days.

(21) Appl. No.: 14/498,298

(22) Filed: Sep. 26, 2014

(65) Prior Publication Data

US 2015/0011020 A1    Jan. 8, 2015

Related U.S. Application Data

(63) Continuation-in-part of application No. 14/227,543, filed on Mar. 27, 2014.
(Continued)

(51) Int. Cl.
*G01N 15/06* (2006.01)
*G01N 33/00* (2006.01)
(Continued)

(52) U.S. Cl.
CPC ........... *G01N 33/521* (2013.01); *G01N 33/02* (2013.01); *G01N 33/5308* (2013.01); *G01N 2001/2866* (2013.01)

(58) Field of Classification Search
CPC ........ G01N 15/06; G01N 33/00; G01N 33/48; G01N 21/00
(Continued)

(56) References Cited

U.S. PATENT DOCUMENTS

| 3,802,842 A | 4/1974 | Lange et al. |
| 4,066,511 A | 1/1978 | Montagnon |

(Continued)

FOREIGN PATENT DOCUMENTS

| CN | 102629689 B | 5/2014 |
| CN | 102016574 B | 9/2014 |

(Continued)

*Primary Examiner* — Brian J. Sines
(74) *Attorney, Agent, or Firm* — Jeffrey Schox

(57) ABSTRACT

A system and method for detecting harmful substances within a consumable sample comprising: receiving a consumable sample at a first chamber of a test container; transforming the consumable sample into a homogenized sample upon processing of the consumable sample; delivering the homogenized sample to a second chamber of the test container, wherein the second chamber is configured to receive the homogenized sample comprises an outlet port; mixing the homogenized sample with a process reagent within the second chamber, thereby producing a dispersion; transmitting a volume of the dispersion to an analysis chamber, of the test container, configured to position a detection substrate proximal the port of the second chamber and comprising a detection window that enables detection of presence of the allergen; and detecting presence of the allergen within the consumable sample by way of an optical sensor configured to detect signals indicative of the allergen through the detection window.

16 Claims, 12 Drawing Sheets

Related U.S. Application Data

(60) Provisional application No. 61/874,590, filed on Sep. 6, 2013, provisional application No. 61/806,425, filed on Mar. 29, 2013.

(51) Int. Cl.
 *G01N 33/52* (2006.01)
 *G01N 33/02* (2006.01)
 *G01N 33/53* (2006.01)
 *G01N 1/28* (2006.01)

(58) Field of Classification Search
 USPC ........ 422/50, 68.1, 400, 401, 402, 403, 404, 422/408, 430, 82.05, 91, 547, 554, 560, 422/561, 55, 4; 436/43, 63, 174, 164, 436/165, 172
 See application file for complete search history.

(56) References Cited

U.S. PATENT DOCUMENTS

| | | | |
|---|---|---|---|
| 4,250,256 A | 2/1981 | Manfred et al. | |
| 4,822,174 A | 4/1989 | Deibel | |
| 5,143,084 A | 9/1992 | MacEmon et al. | |
| 5,217,905 A | 6/1993 | Marchand et al. | |
| 5,256,372 A | 10/1993 | Brooks et al. | |
| 5,504,013 A | 4/1996 | Senior | |
| 6,136,549 A | 10/2000 | Feistel | |
| 6,136,610 A | 10/2000 | Polito et al. | |
| 6,180,335 B1 | 1/2001 | Wilkins et al. | |
| 6,319,466 B1 | 11/2001 | Markovsky et al. | |
| 6,528,323 B1 | 3/2003 | Thayer et al. | |
| 6,616,893 B1 | 9/2003 | Pham | |
| 7,098,040 B2 | 8/2006 | Kaylor et al. | |
| 7,220,597 B2 | 5/2007 | Zin et al. | |
| 7,267,799 B1 | 9/2007 | Borich et al. | |
| 7,371,582 B2 | 5/2008 | Nahm et al. | |
| 7,507,374 B2 | 3/2009 | Gould et al. | |
| 7,527,765 B2 | 5/2009 | Royds | |
| 7,585,529 B2 | 9/2009 | Villar et al. | |
| 7,776,266 B2 | 8/2010 | Royds | |
| 7,932,099 B2 | 4/2011 | Egan et al. | |
| 8,211,715 B1 | 7/2012 | Royds | |
| 8,278,091 B2 | 10/2012 | Rutter et al. | |
| 8,632,730 B2 | 1/2014 | Petrilla et al. | |
| 9,005,551 B2 | 4/2015 | Chen et al. | |
| 2003/0186458 A1 | 10/2003 | DiCesare et al. | |
| 2004/0018575 A1* | 1/2004 | Rappin | B01L 3/502 435/7.92 |
| 2004/0132091 A1* | 7/2004 | Ramsey | A61B 10/007 435/7.1 |
| 2004/0265234 A1 | 12/2004 | Morimatsu et al. | |
| 2005/0255533 A1 | 11/2005 | Dantini et al. | |
| 2006/0051237 A1 | 3/2006 | Wang et al. | |
| 2006/0292035 A1 | 12/2006 | Gould et al. | |
| 2007/0047382 A1* | 3/2007 | McCurdy | B01F 1/0011 366/153.1 |
| 2007/0054414 A1* | 3/2007 | Burgess-Cassler | B01L 3/5023 436/514 |
| 2008/0171397 A1 | 7/2008 | Hardcastle et al. | |
| 2009/0047691 A1 | 2/2009 | Huwig et al. | |
| 2010/0167309 A1 | 7/2010 | Chandler | |
| 2010/0210033 A1 | 8/2010 | Scott | |
| 2010/0222224 A1 | 9/2010 | Suni et al. | |
| 2010/0317033 A1 | 12/2010 | Abdel | |
| 2011/0059550 A1 | 3/2011 | Haik | |
| 2012/0264232 A1 | 10/2012 | Kramer et al. | |
| 2014/0033809 A1 | 2/2014 | Bransky et al. | |
| 2014/0072980 A1 | 3/2014 | Lansing | |
| 2014/0120563 A1 | 5/2014 | Ozcan et al. | |
| 2014/0186880 A1 | 7/2014 | Lowenkamp, Jr. | |

FOREIGN PATENT DOCUMENTS

| | | |
|---|---|---|
| EP | 1034429 B1 | 11/2003 |
| WO | 2011039198 A2 | 4/2011 |
| WO | 2012078455 A1 | 6/2012 |

\* cited by examiner

Elevation Schmatic

Isometric View

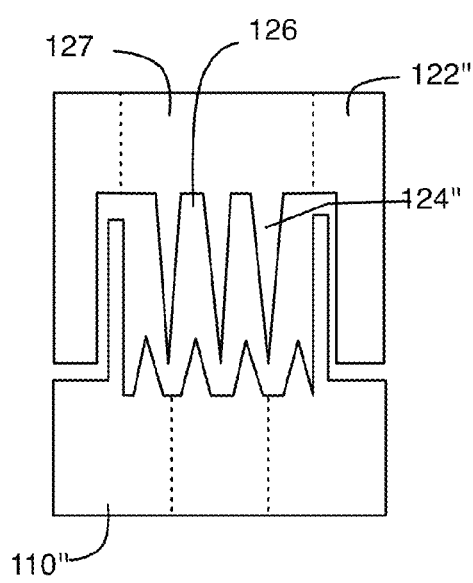
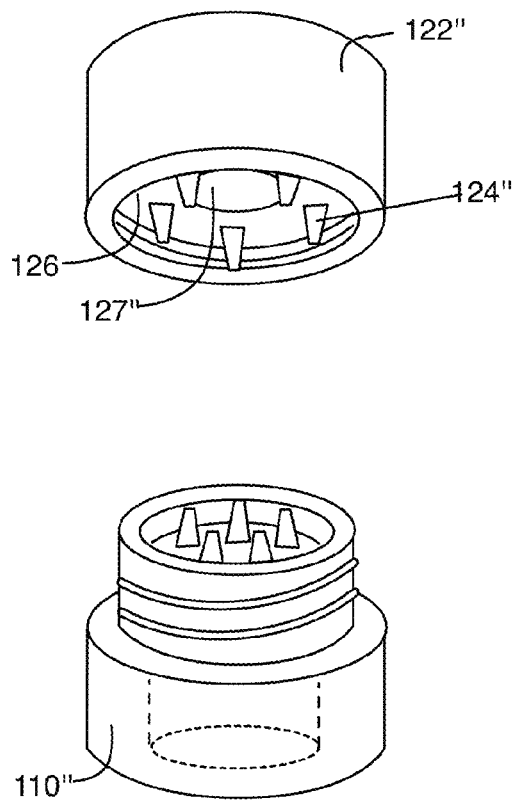
Elevation Schmatic
FIGURE 4A
Isometric View
FIGURE 4B

Pre-processing Image of 150

Post-processing Image of 150

SYSTEM AND METHOD FOR DETECTION OF TARGET SUBSTANCES

CROSS-REFERENCE TO RELATED APPLICATIONS

This application is a Continuation-In-Part application of U.S. application Ser. No. 14/227,543, filed on 27 Mar. 2014, which claims the benefit of U.S. Provisional Application Ser. No. 61/874,590, filed on 6 Sep. 2013, and U.S. Provisional Application Ser. No. 61/806,425, filed on 29 Mar. 2013, which are each incorporated herein in their entirety by this reference.

TECHNICAL FIELD

This invention relates generally to the consumer assay device field, and more specifically to an improved system and method for detection of target substances within a consumable.

BACKGROUND

A wide variety of consumables (e.g., foods, beverage, cosmetics, etc.) contain contaminants, toxins, allergens, and/ or other substances that are of interest to all or specific types of consumers. In particular, in recent years, an increase in the number of consumers with an identified allergy (e.g., gluten allergy, dairy allergy, fish allergy, nut allergy, soy allergy, cosmetic allergy, etc.) has contributed to a number of products that omit ingredients having an associated allergen; however, such consumers are still at risk for consuming items with a harmful substance when the items do not have adequate labeling or documentation. Various systems and methods exist for detection of toxins and harmful substances present in a sample; however, current systems and methods are deficient due to one or more of: a time-intensive manner of receiving test results, a labor-intensive manner of receiving test results, a non-automated manner of processing samples, system bulk, system non-portability, and other factors that contribute to inconveniencing a consumer using such systems.

Due to these and other defects of current systems and methods for detecting harmful substances in consumables, there is thus a need for and improved system and method for detecting target substances. This invention provides such a system and method.

BRIEF DESCRIPTION OF THE FIGURES

FIGS. 4A and 4B depict second variations and examples of a portion of a system for detection of harmful substances;

DESCRIPTION OF THE PREFERRED EMBODIMENTS

The following description of preferred embodiments of the invention is not intended to limit the invention to these preferred embodiments, but rather to enable any person skilled in the art to make and use this invention.

1. System

Figure 1:
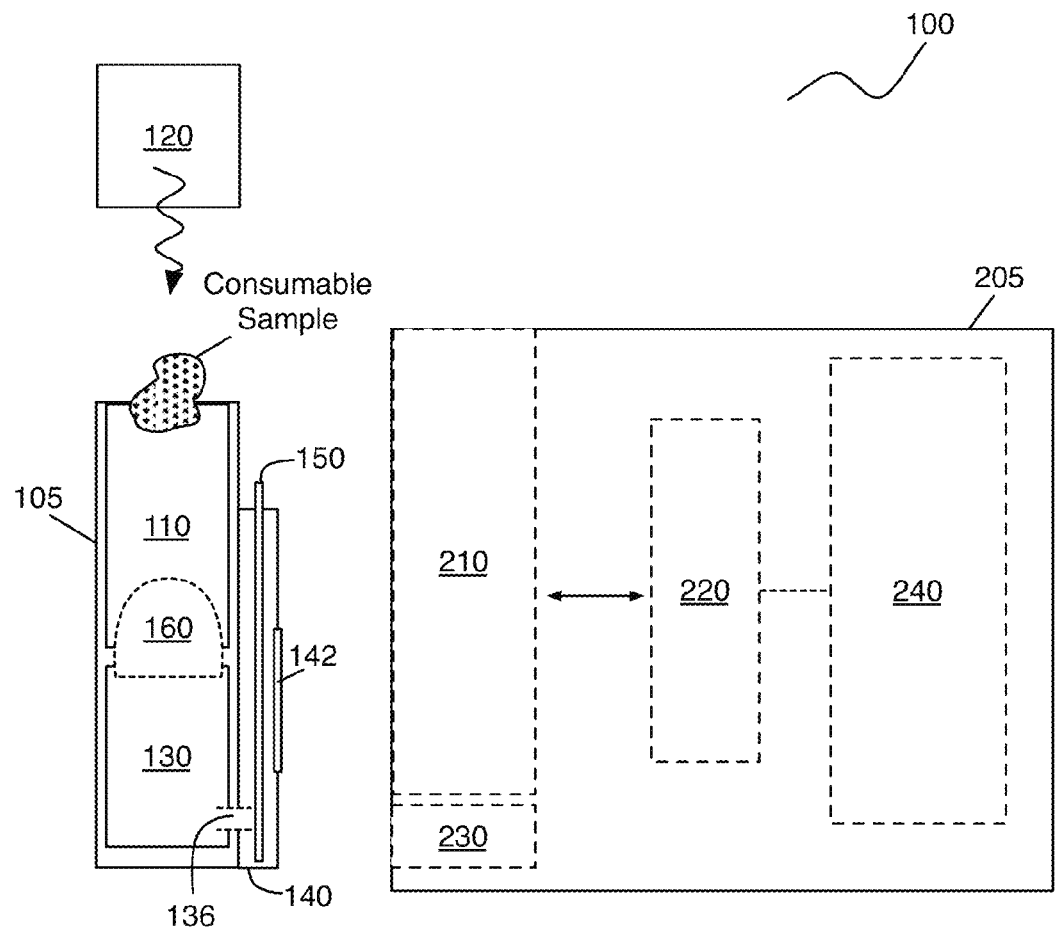
FIG. 1 depict an embodiment of a system for detection of harmful substances.

As shown in FIG. 1, an embodiment of a system 100 for detecting a target substance in a consumable sample comprises: a test container 105 and an analysis device 205 configured to detect presence of the harmful substance at the test container 105. In an embodiment, the test container 105 includes: a first chamber 110 for receiving the consumable sample, a driving element 120 configured to generate a homogenized sample upon processing of the consumable sample, a second chamber 130 configured to receive the homogenized sample and combine it with a process reagent to produce a dispersion, and analysis chamber 140 configured to expose the dispersion to a detection substrate 150 for detection of the harmful substance. In an embodiment, the analysis device 205 includes: a receiving port 210 configured to receive the test container 105, an optical sensing subsystem 220 configured to enable detection of presence of the harmful substance at the detection substrate 150, a mixing module 230 configured to mix the homogenized sample with a process reagent, and a processing and control system 240 configured to receive and process signals from the optical sensing subsystem 220, thereby producing an output indicative of presence of the harmful substance in the consumable sample.

The system 100 functions to receive and process a sample of a consumable (e.g., food, beverage, cosmetic, etc.) in order to enable detection of one or more harmful substances within the sample. In examples, the harmful substances can include any one or more of: an allergen (e.g., gluten allergen, a dairy-derived allergen, a nut allergen, a fish allergen, an egg-derived allergen, etc.) a toxin, a bacterium, a fungus, a pesticide, a heavy metal, a chemical or biological compound (e.g., a fat, a protein, a sugar, a salt, etc.), and any other suitable harmful substance. The system 100 is preferably configured to impose minimal requirements upon a consumer using the system 100, in terms of labor-intensiveness, time-intensiveness, and cost-intensiveness. As such, the system 100 is preferably configured to automatically or semi-automatically process the sample in a manner that is intuitive to the consumer, and to quickly provide information regarding presence of the harmful substance(s) within the sample. The system 100 is preferably configured to be portable and compact, such that the user can conveniently carry the system 100 during his/her daily life (e.g., to establishments); however, in some alternative variations, the system 100 can be configured to be non-portable and/or non-compact. Preferably, the system 100 has reusable and disposable components, and in some variations portions of the system 100 are configured to be single-use (e.g., the test container(s), portions of a test container) while other portions of the system 100 are configured to be reusable (e.g., the analysis device). However, in other variations, the system 100 can include only reusable components or only disposable components.

In an example workflow, the system 100 is configured to receive a sample at a first chamber of a test container, to homogenize the sample, and to mix the homogenized sample with at least one process reagent to enable detection of one or more harmful substances within the sample at an analysis device. In the example workflow, a user of the system 100 would deposit the sample into the test container, perform a small amount of labor to facilitate homogenization of the sample, and place the container in the analysis device for further processing and analysis of the sample, such that the user has minimal interaction with the system 100 in generating an output. In another example workflow, the system 100 is configured to receive a sample at a first chamber of a test container, to homogenize the sample, and to mix the homogenized sample with at least one process reagent to enable detection of one or more harmful substances within the sample at an analysis device. In this example workflow, the system 100 is configured to receive and process a sample without any labor required by a user, in order to enable detection of a target substance within the sample in a fully-automated manner. As such, the system is preferably configured to facilitate implementation of the method 300 described in Section 2 below; however, the system 100 can additionally or alternatively be configured to perform any other suitable method.

1.1 System—Test Container

As noted above and shown in FIGS. 1 and 2A-2B, in an embodiment, the test container 105 includes: a first chamber 110 for receiving the consumable sample, a driving element 120 configured to generate a homogenized sample upon processing of the consumable sample, a second chamber 130 configured to receive the homogenized sample and combine it with a process reagent to produce a dispersion, and analysis chamber 140 configured to expose the dispersion to a detection substrate 150 for detection of the harmful substance.

The first chamber 110 functions to receive and facilitate processing (e.g., homogenization) of a consumable sample that the user intends to analyze for presence of a harmful substance. In an embodiment, the first chamber 110 preferably comprises a consumable reception opening 112 configured to receive the consumable sample from the user, and a second opening 114 configured to deliver a homogenized sample generated from the consumable sample into the second chamber 130 for further processing.

The consumable reception opening 112 can be configured to passively receive the consumable sample, or can additionally or alternatively be configured to actively facilitate reception of the consumable sample, for instance, by transmitting a positive/negative pressure at the consumable reception opening 112 that drives the consumable sample into the first chamber 110, by providing a mechanism (e.g., scooping mechanism, suction mechanism) that guides the consumable sample into the consumable reception opening 112, and/or by providing any other suitable mechanism for active delivery of the consumable sample into the first chamber 110. The consumable reception opening 112 is preferably at a superior portion of the first chamber 110, in the orientation shown in FIGS. 2A and 2B, such that gravity facilitates transfer of the consumable sample, during processing, toward a second chamber 130 inferior to the first chamber 110; however, the consumable reception opening 112 can alternatively be configured at any other suitable location along the length of the first chamber 110. Additionally or alternatively, transfer of samples and/or process reagents throughout the system 100 can be facilitated with pressurization or any other suitable means of driving material (e.g., such that gravitational force is not required). Furthermore, in examples, the consumable reception opening can include features (e.g., a sloped entryway into the first chamber 110, a wide mouth relative to other portions of the interior of first chamber 110) that facilitate reception of the consumable sample. Additionally or alternatively, the consumable reception opening 112 and/or any other portion of the first chamber 110 can include a feature that facilitates control of an amount of a consumable sample that is processed using the test container 105, prior to and/or after reception of the consumable sample within the first chamber 110. For instance, the first chamber can comprise a maximum and/or minimum fill line to guide delivery of the consumable sample into the first chamber 110 between a maximum and/or minimum range of amounts. In another example, portions of the test container 105 can be configured to exclude or accommodate a larger than desired volume of a consumable sample (e.g., by distributing excess volumes of the consumable sample into another portion of the system 100, or by expelling excess volumes of the consumable sample from the system 100). In examples, the consumable reception opening 112 can have a diameter or width between 10 and 20 mm; however, the consumable reception opening can alternatively have any other suitable dimensions.

The consumable sample is preferably a food sample potentially containing a harmful substance (e.g., an allergen), and is preferably an unprocessed food sample, such that the user can gather an insubstantial volume of a food substance that he/she intends to consume for a meal, and deliver it into the consumable reception opening 112 of the test container 105 for processing and analysis. In this example, the food sample can comprise a mixture of different food items (e.g., different components of an entrée), can comprise a single food item (e.g., a single component of an entrée), and/or can comprise a sequence of different food items (e.g., a sequence of components from an entrée). The food sample can be cored, spooned, tweezed, and/or processed from a bulk volume of food in any other suitable manner. However, in variations, the consumable sample can include any one or more of a: beverage sample (e.g., volume of a mixed drink), cosmetic substance (e.g., volume of makeup, volume of lotion, volume of fragrance, volume of soap, etc.), and any other sample potentially containing a substance that is harmful to the user. In variations, the consumable sample can have a volume of between 1 and 7 mL prior to processing within the first chamber 110; however, the consumable sample can alternatively have any other suitable volume.

The second opening 114 functions to deliver a homogenized sample generated from the consumable sample into the second chamber 130 for further processing. The second opening 114 is preferably at an inferior portion of the first chamber 110 relative to the consumable reception opening, in the orientation shown in FIGS. 2A and 2B, such that gravity facilitates transfer of the consumable sample, during processing, toward a second chamber 130 inferior to the first chamber 110; however, the second opening 114 can alternatively be configured at any other suitable location along the length of the first chamber 110. Furthermore, in examples, the second opening 114 can include features (e.g., a sloped entryway into the second chamber 130, a wide mouth relative to other portions of the interior of first chamber 110) that facilitate delivery of the consumable sample out of the first chamber 110. In examples, the second opening 114 can have a diameter or width between 10 and 20 mm; however, the consumable reception opening can alternatively have any other suitable dimensions.

The first chamber 110 preferably defines an internal enclosed cavity open only at the consumable reception opening 112 and the second opening 114, in order to facilitate processing of the consumable sample, within the first chamber 110, in a desired direction. However, the first chamber 110 can additionally or alternatively include venting and/or metering features that facilitate processing of the consumable sample in a controlled manner. The volume of the first chamber 110 is preferably substantially small, in order to contribute to compactness of the test container, and in order to accommodate a small volume of the consumable sample, such that the user does not feel as though he/she is sacrificing a sufficient portion of his/her food. In variations, the first chamber 110 has an internal volume of between 1 and 7 mL between the consumable reception opening 112 and the second opening 114; however, the first chamber 110 can alternatively define any other suitable volume.

Figure 2A:
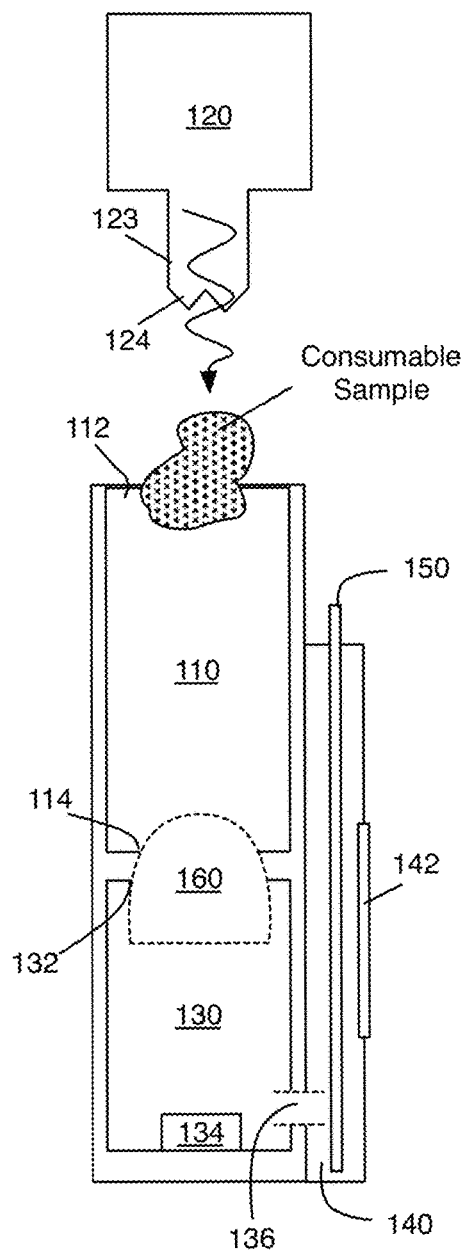
FIGS. 2A and 2B depict embodiments and variations of a portion of a system for detection of harmful substances.
Figure 2B:
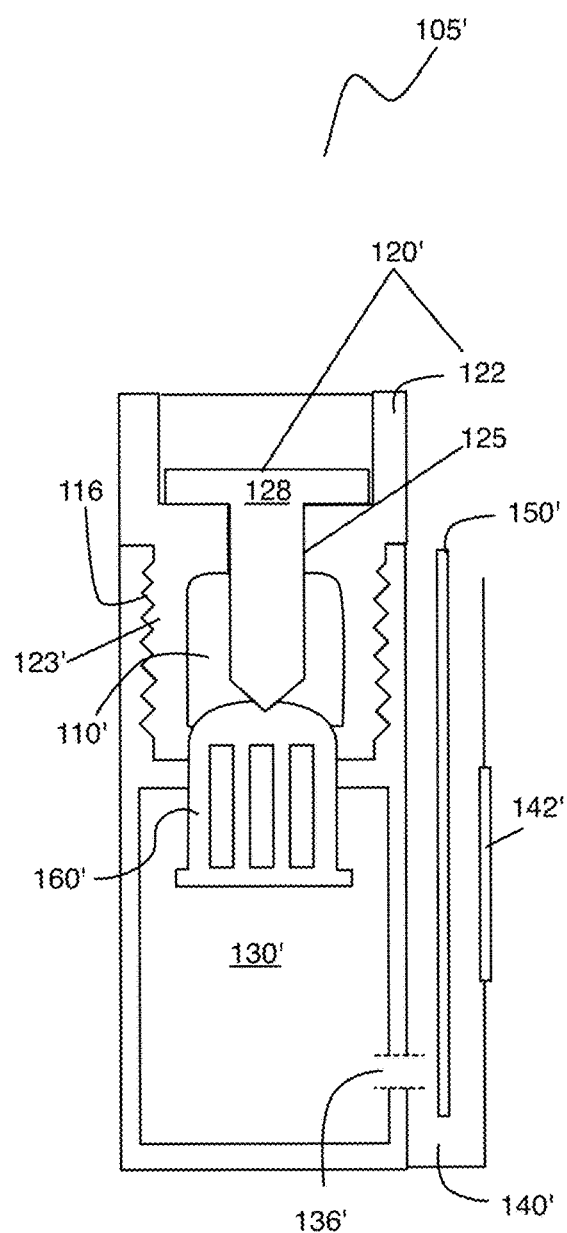

In morphology, the internal cavity of the first chamber 110 preferably has a uniform cross section over a majority of the length of the first chamber 110, in order to facilitate processing of the consumable sample in a uniform manner throughout the length of the first chamber 110; however, the cross section of the first chamber 110 can alternatively be non-uniform. Additionally, the internal cavity of the first chamber 110 preferably includes features that facilitate processing of the consumable sample by other elements of the test container 105 (e.g., the driving element 120, as described in further detail below. As such, in one example, an interior portion (e.g., wall) and/or an exterior portion (e.g., exterior surface) of the first chamber 110 can include threads 116, as shown in FIG. 2B, that facilitate screwing of a driving element 120 within/about the first chamber 110 in processing the consumable sample toward the second opening 114. In another example, an interior portion or exterior portion (e.g., wall, surface) of the first chamber 110 can be substantially smooth and/or have low friction to facilitate sliding of a driving element 120 between the consumable reception opening 112 and the second opening 114 of the first chamber 110. The first chamber 110 can, however, include any other suitable features that facilitate processing of the consumable sample in cooperation with another element (e.g., a driving element) of the system 110. For instance, the first chamber 110 can include a fill line configured to guide a user in providing a desired amount of the consumable sample (e.g., such that an amount of the consumable sample provided by the user is above a lower critical limit and below an upper critical limit).

Figures 3A, 3B:
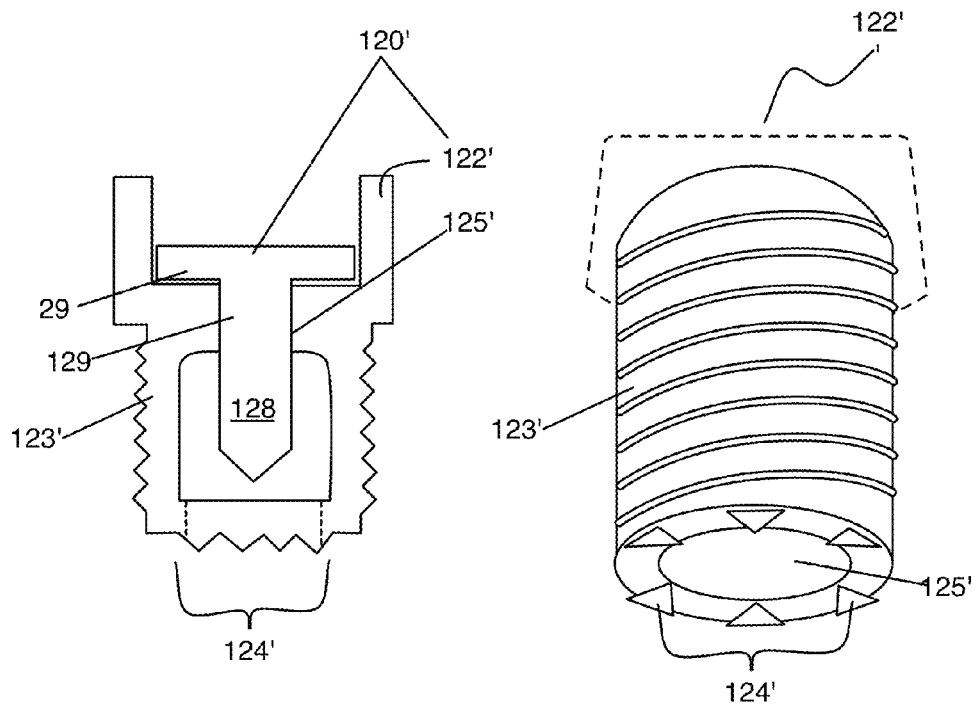
FIGS. 3A and 3B depict first variations and examples of a portion of a system for detection of harmful substances.

The driving element 120 functions to interact with the first chamber and to facilitate generation of a homogenized sample upon processing of the consumable sample toward the second opening 114 of the first chamber 110. As such, the driving element 120 preferably has a morphological form that complements or mates with a morphological form of the first chamber 110 (e.g., an interior morphology of the first chamber, an exterior morphology of the first chamber) in providing a mechanism that transforms the consumable sample into a homogenized sample. Preferably, the driving element 120 has a portion (e.g., shaft) that interacts with an interior portion of the first chamber 110, as shown in FIGS. 2B and 3A-3B, wherein relative motion between the first chamber 110 and the driving element 120 is guided (e.g., constrained) by the morphological forms of the first chamber 110 and the driving element 120. In one variation, the driving element 120 includes a grinder 122 and a plunger 128, as described below and shown in FIGS. 2A-2B and 3A-3B, however, other variations of the driving element 120 can adapt elements or features of the grinder 122/plunger 128 in enabling processing of the consumable sample, and/or be configured in any other suitable manner.

The grinder 122 functions to grind the consumable sample within the first chamber 110 during relative motion between the driving element 120 and the first chamber 110, in order to produce a homogenized sample with approximately uniformly sized particles. The homogenized sample is then distributed into the second chamber 130 for further processing with a process reagent, and analysis using a detection substrate 150. In one variation, the grinder 122 includes a shaft 123 and a set of protrusions 124 coupled to the shaft 123, and is configured to grind the consumable sample during processing of the consumable sample between the consumable reception opening 112 and the second opening 114 of the first chamber 110. Preferably, the shaft 123 is configured to translate within the interior portion of the first chamber 110 (e.g., with sliding motion, with rotational motion that produces translation), and the set of protrusions 124 is configured to grind up the consumable sample as the shaft 123 rotates and/or translates within the first chamber 110. As such, translation/rotation of the grinder 122 relative to the first chamber 110 moves portions of the consumable sample between protrusions of the set of protrusions 124, thereby grinding the consumable sample. The shaft 123 can also include a channel 125 (e.g., a channel concentrically aligned with the shaft) to accommodate a plunger that enables driving of the homogenized sample from the first chamber 110 to the second chamber 130; however, the shaft 123 can alternatively omit a channel 125 and be substantially solid. In this variation, the set of protrusions 124 preferably includes protrusions having sharp points and/or a rough surface, in order to facilitate grinding of the consumable sample. Furthermore, the set of protrusions 124 can be arranged in a pattern (e.g., a radial pattern, a rectangular pattern) with respect to a surface of the shaft 123. Furthermore, the set of protrusions 124 preferably has a small inter-protrusion spacing (e.g., between 0.1 mm to 0.5 mm). However, the set of protrusions 124 can alternatively be arranged in a random manner and/or in any other suitable manner.

In one example of this variation, as shown in FIGS. 3A-3B, the grinder 122' includes an set of protrusions 124' arranged in a uniform radial distribution at an inferior surface of a shaft 123' having a concentric channel 125', wherein each protrusion defines a wedge-shaped footprint having a sharp point pointing toward the channel 125' of the shaft. In this example, the set of protrusions 124' includes 6 wedge-shaped protrusions; however, variations of this example can include any other suitable number of protrusions (e.g., between 4 and 12 protrusions) defining any other suitable morphology. Furthermore, in this example, the shaft includes exterior threads configured to enable translation of the shaft 123 within the first chamber 110', as the shaft rotates in cooperation with mating threads 116 within the interior of the first chamber 110'. However, variations of this example of the grinder 122' can include protrusions having a non-uniform and/or a non-radial arrangement. Furthermore, the shaft and the first chamber 110 can be alternatively configured such that mating threads 116 at an exterior surface of the first chamber are configured to mate with a portion of the grinder 122' in order to facilitate relative motion between the grinder 122' and the first chamber 110 during grinding.

In another variation, as shown in FIGS. 4A and 4B, the grinder 122 includes a set of protrusions 124 at an interior surface 126 of the grinder 122, wherein the interior surface 126 is configured to be parallel to a corresponding surface within the first chamber 110. As such, in this variation, translation and/or rotation of the grinder 122 about/within the first chamber 110 moves portions of the consumable sample between protrusions of the set of protrusions 124, thereby grinding the consumable sample. The grinder 122 in this variation includes a plunger opening 127 configured to accommodate a plunger that enables driving of the homogenized sample from the first chamber 110 to the second chamber 130; however, the grinder 122 can alternatively omit a plunger opening 127 and be substantially solid. In this variation, the set of protrusions 124 preferably includes protrusions having sharp points and/or a rough surface, in order to facilitate grinding of the consumable sample. Furthermore, the set of protrusions 124 can be arranged in a pattern (e.g., a radial pattern, a rectangular pattern) with respect to the interior surface 126 of the grinder 122 (e.g., about an opening 127 in the grinder 122), or arranged in any other suitable manner.

In one example of this variation, as shown in FIGS. 4A and 4B, the grinder 122" includes an set of protrusions 124" arranged in a uniform radial distribution at an interior surface having a concentric plunger opening 127", wherein each protrusion defines a wedge-shaped footprint having a sharp point pointing toward the plunger opening 127" of the interior surface 126". In this example, the set of protrusions 124" includes 5 wedge-shaped protrusions; however, variations of this example can include any other suitable number of protrusions (e.g., between 4 and 12 protrusions) defining any other suitable morphology. Furthermore, in this example, the grinder 122" includes interior threads configured to enable translation of the grinder 122" about an exterior portion of the first chamber 110", as the shaft rotates in cooperation with mating threads at the exterior portion of the first chamber 110".

Other variations of the grinder 122 can additionally or alternatively operate using any other suitable mechanism. For instance, the grinder 122 can operate by one or more of: forcing the consumable sample through a screen (e.g., a mesh screen), crushing the consumable sample (e.g., as in a pill crusher), processing the consumable sample (e.g., with a blade), grinding the consumable sample as in a mortar-and-pestle), and in any other suitable manner.

The plunger 128 functions to facilitate driving of homogenized portions of the consumable sample into the second chamber 130 after and/or during processing by the grinder 122. In variations of the test container 105 including a diaphragm 160, the plunger 128 can additionally or alternatively function to transition the diaphragm 160 between a first configuration and a second configuration, as described in further detail below. In a variation shown in FIG. 3A, the plunger 128 can include a plunger shaft 129 and a stop 29, wherein the plunger shaft 129 is configured to pass through a channel 125 or plunger opening 127 of the grinder 122, in order to facilitate driving of the homogenized sample into the second chamber 130. The stop 29 is then configured to constrain a range of motion of the plunger 128, such that the plunger cannot pass entirely into the first chamber in an uncontrolled manner. Preferably the plunger shaft 129 is a cylindrical shaft; however, the plunger shaft 129 can alternatively have any other suitable cross-section or profile configured to facilitate driving of the homogenized sample into the second chamber 130, in cooperation with the grinder 122. In particular, an inferior portion of the plunger shaft 129 can be blunt (e.g., hemispherical, planar), sharp (e.g., conical, pyramidal), or have any other suitable morphology for driving of the homogenized sample into the second chamber 130. The stop 29 preferably has a larger governing dimension than the plunger shaft 129 to provide the constrained range of motion; however, in other variations, the stop 29 can include protrusions (e.g., tabs) extending from a surface of the plunger shaft 129, thereby obstructing motion of the plunger shaft 129 into the channel 125/plunger opening 127 past the stop 29. The plunger 128 can be coupled to the grinder, can be distinct from the grinder 122, or can be configured to interface with the grinder 122 in any other suitable manner. In one example, the plunger 128 includes a cylindrical plunger shaft 129 configured to slide within a channel 125/plunger opening 127 of the grinder 122, and the stop 29 comprises a plate coupled to a superior portion of the plunger shaft 129, having a diameter wider than that of the plunger shaft 129 to constrain a range of motion of the plunger shaft 129.

In other variations, elements of the grinder 122 can additionally or alternatively be distributed within the first chamber 110, such that the first chamber 110 includes elements that actively enable grinding of the consumable sample. For instance, an inferior surface of the first chamber 110 can include at least a subset of the set of protrusions 124, such that movement of the grinder 122 processes the consumable sample in cooperation with protrusions within the first chamber. In some variations, a plunger 128 can be replaced by a driving module (e.g., configured to provide positive and/or negative pressure within the test container, configured to centrifuge the test container, etc.) that facilitates delivery of the homogenized sample throughout the test container in a controlled manner. In still other variations, however, the driving element 120 can omit the grinder 122, the plunger 128, and/or any other features configured to process a solid and/or non-homogenous consumable sample (e.g., beverage, cosmetic, etc.), which would not require grinding within a first chamber 110 prior to reception at a second chamber. As such, in some variations of the system 100, the first chamber 110, the driving element 120, and/or the second chamber 130 can be configured in manners that are appropriate to processing of consumable samples, based upon the form(s) of the consumable samples.

The second chamber 130 functions to receive the homogenized sample after processing within the first chamber 110, to facilitate combination of the homogenized sample with a process reagent to produce a dispersion, and to facilitate delivery of the dispersion from the second chamber 130 for further analysis to detect a harmful substance. Preferably, the second chamber 130 includes a sample reception opening 132 and an outlet port 136 configured to facilitate delivery of the dispersion to a detection substrate, as shown in FIG. 2A. In some variations, the second chamber 130 can further include a mixing element 134 configured to cooperate with a mixing module (e.g., of an analysis device 205 in communication with the test container), to facilitate mixing of the homogenized sample with the process reagent in the second chamber 130. However, the second chamber 130 can additionally or alternatively comprise any other suitable elements and/or be configured in any other suitable manner for generation of a dispersion from the homogenized sample.

The second chamber 130 is preferably configured to couple to the first chamber 110, and in variations, can comprise a unitary construction with the first chamber, can be physically coextensive with the first chamber 110, and/or can be coupled to the first chamber 110 in any other suitable manner. Furthermore, the second chamber 130 is preferably inferior to the first chamber 110, such that gravity facilitates transfer of the homogenized sample from the first chamber 110 toward the second chamber 130 in the orientation shown in FIG. 2A. However, the second chamber can alternatively be configured adjacent to or in any other suitable location relative to the first chamber 110 in alternative variations of the system 100.

The sample reception opening 132 can be configured to passively receive the homogenized sample, or can additionally or alternatively be configured to actively facilitate reception of the homogenized sample, for instance, by transmitting a positive/negative pressure at the sample reception opening 132 that drives the homogenized sample into the second chamber 130, by providing a mechanism (e.g., scooping mechanism) that guides the homogenized sample into the sample reception opening 132, and/or by providing any other suitable mechanism for active delivery of the homogenized sample into the second chamber 130. Additionally or alternatively, portions of the test container 105 and/or system 100 can be configured to facilitate delivery of contents from the first chamber 110 into the second chamber 130. For instance, a portion of the driving element 120 (e.g., the plunger 128) can comprise a module (e.g., syringe pump, fluid delivery element) that applies positive pressure and/or delivers a wash solution from the first chamber 110 to the second chamber 130, in order wash portions of the homogenized sample into the second chamber 130. The sample reception opening 132 is preferably at a superior portion of the second chamber 130, in the orientation shown in FIG. 2A, such that gravity facilitates transfer of the homogenized sample, during processing, into the second chamber 130 in cooperation with the driving element 120; however, the sample reception opening 132 can alternatively be configured at any other suitable location along the length of the second chamber 130. Furthermore, in examples, the sample reception opening can include features (e.g., a sloped entryway into the second chamber 130, a wide mouth relative to other portions of the interior of second chamber 130) that facilitate reception of the homogenized sample. In examples, the consumable reception opening 112 can have a diameter or width between 10 and 20 mm; however, the sample reception opening can alternatively have any other suitable dimensions.

In variations, the sample reception opening 132 is preferably configured to facilitate transitioning of a diaphragm 160, configured to facilitate delivery of the homogenized sample into the second chamber 130, between a first configuration and a second configuration, as described in further detail below; however, the sample reception opening 132 can alternatively be configured to facilitate delivery of the homogenized sample into the second chamber 130 from the first chamber 110 without a diaphragm 160, for instance, by way of a valve (e.g., one-way valve, two-way valve) configured between the first chamber 110 and the second chamber 130. Alternatively, the sample reception opening 132 can be configured to directly transfer the homogenized sample from the first chamber 110 to the second chamber 130 without any intermediate element(s).

Figure 5:
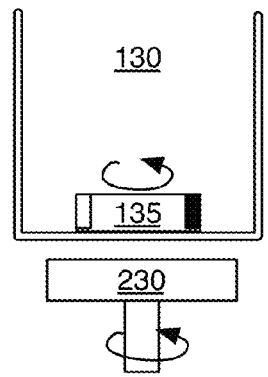
FIG. 5 depicts an example of a portion of a system for detection of harmful substances.

In some variations, the second chamber 130 can include a mixing element 134 that functions to facilitate mixing of the homogenized sample with a process reagent within the second chamber 130. The mixing element 134 can be disposed within the second chamber 130, and/or can be coupled to the second chamber 130 in any other suitable manner. The mixing element 134 is preferably configured to cooperate with a mixing module 230 of an analysis device 205, as described in further detail below, such that the mixing element 134 and the mixing module 230 complement each other to provide a mixing mechanism within the second chamber 130; however, variations of the system 100 can entirely omit the mixing element 134 and/or the mixing module 230 and facilitate combination of the homogenized sample with the process reagent in any other suitable manner (e.g., the process reagent can be combined with the consumable sample during processing within the first chamber 110). In variations, the mixing element 134 can provide any one of: a magnetically-driven mechanism of mixing, an ultrasonic mechanism of mixing, a vibration-based mechanism of mixing (e.g., mechanically driven, acoustically driven), a rocking motion, a spinning-based mechanism of mixing (e.g., by forming a vortex), a shaking-based mechanism of mixing, and any other suitable mechanism of mixing. In an example, as shown in FIG. 5, the mixing element 134 comprises a magnet 135 (e.g., magnetic stir bar) configured within the second chamber 130 that is configured to magnetically couple to a complementary magnet of a mixing module 230. In the example, the complementary magnet can be coupled to a spinning motor, thereby producing rotation at the magnet 135 within the second chamber 130. In variations of the example, the magnet 135 can comprise a permanent magnet and/or an electromagnet. Furthermore, the magnet 135 can be a distinct element within the second chamber 130, or can additionally or alternatively be coupled to or integrated with a diaphragm 160 configured to access the second chamber 130, as described below. Furthermore, variations of the example can include any suitable number of magnets 135 of the second chamber 130.

In variations, the second chamber 130 can be prepackaged with the process reagent, such that the homogenized sample is automatically brought into contact with the process reagent upon transmission between the first chamber 110 and the second chamber 130. Alternatively, the second chamber 130 and/or any other suitable portion of the test container 105 can comprise or be coupled to a fluid delivery module for reception of the process reagent and combination of the process reagent with the homogenized sample or the consumable sample. For instance, the process reagent can be delivered from a module integrated with one or more portions of the driving element 120 (e.g., from the plunger 128, from beneath the grinder 122), such that the process reagent does not originate from within the second chamber 130. As such, mixing of the consumable sample with a process reagent can occur prior to grinding of the consumable sample by a driving element 120.

The process reagent preferably includes an extraction solution configured to extract at least one analyte, associated with a harmful substance, from the homogenized sample, that can be detected at a detection substrate and used to indicate presence of the harmful substance. In an example for gluten detection, the extraction solution can contain 2-mercaptoethanol, or tris(2-carboxyethyl)phosphine, which operates by reducing disulfide prolamin crosslinking in a sample, and solubilizes proteins in the sample to facilitate detection. The extraction solution can additionally or alternatively contain guanidine hydrochloride, or N-lauroylsarcosine, or other disaggregating agents. In variations for other allergens, the extraction solution can comprise ethanol for a dairy-derived allergen (e.g., lactose), a parvalbumin extraction solution for a fish-derived allergen, an ara-h2 extraction solution for a nut derived allergen, an egg protein extraction solution for an egg-derived allergen (e.g., ovomucoid protein, ovalbumin protein, ovotransferrin protein, lysozyme protein), a tropomyosin extraction solution for a shellfish-derived allergen, and/or any other suitable extraction solution for any other harmful substance. Furthermore, variations of the process reagent(s) can additionally or alternatively include any one or more of: a reagent for lysing of a sample, a reagent for solubilization of a sample, a reagent for buffering of a sample, a reagent for dilution of a sample, and any other suitable reagent(s). For instance, in some variations, extraction and dilution of a sample to generate a dispersion can involve a first process reagent for extraction (e.g., an alcohol-based solution for extraction of gluten), and a second process reagent for dilution of a sample processed with the first process reagent, such that the dispersion has appropriate characteristics for assessment at a detection substrate 150.

The outlet port 136 functions to facilitate delivery of a controlled volume (and/or rate of flow) of the dispersion, from the second chamber 130, to an analysis chamber 140 for detection of the harmful substance(s) within the consumable sample. The outlet port 136 is preferably situated at an inferior portion of the second chamber, an example of which is shown in FIG. 2B, in order to facilitate delivery of the dispersion from the second chamber at least in part by gravity. However, the outlet port 136 can alternatively be configured at any suitable location relative to the second chamber. The outlet port 136 preferably allows a volume of the dispersion to be transmitted to a detection substrate 150 at an analysis chamber 140 in communication with the port, wherein the volume of the dispersion is configured so as to provide an adequate amount of the dispersion without flooding the detection substrate.

Figure 6A:
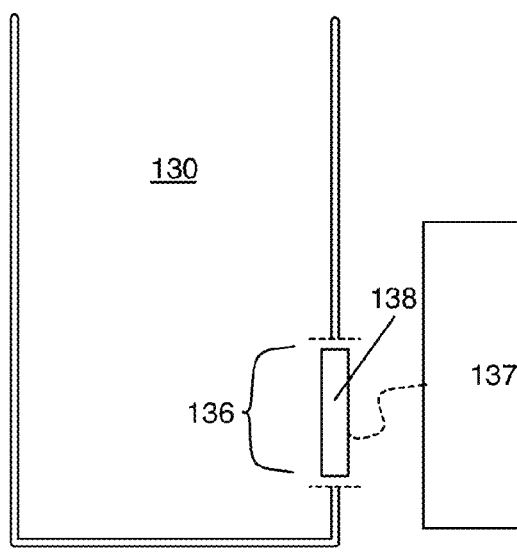
FIGS. 6A and 6B depict variations of a valve mechanism in an embodiment of a system for detection of harmful substances.
Figure 6B:
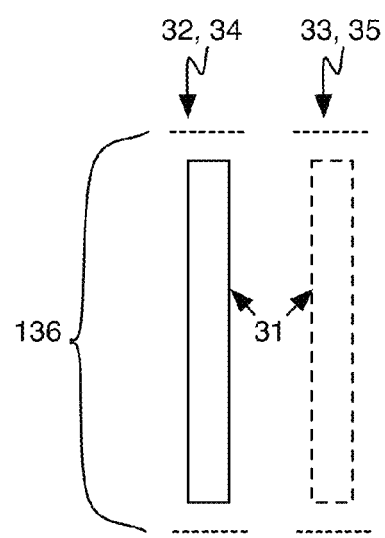

While the outlet port 136 can be configured to passively facilitate delivery of the dispersion to a detection substrate at the analysis chamber 140, variations of the system 100, as shown in FIG. 6A, can include an actuation system 137 configured to provide or meter a controlled volume of the dispersion to the analysis chamber 140. In one variation, an actuation system 137 coupled to the outlet port 136 can include a valve 138 that can be controllably opened and/or closed in order to dispense the dispersion into the analysis chamber 140 with a controlled volume and/or at a controlled time point. In an example, the valve 138 can include a rod 31 (e.g., needle) that is biased to be closed in a first valve configuration 32 and configured to open in a second valve configuration 33, wherein transitioning between the first valve configuration 32 and the second valve configuration 33 can be controlled by actuators (e.g., solenoids, etc.) of the test container 105 and/or analysis device 205, pressurization of the test container 105 (e.g., using a pneumatic mechanism), and/or in any other suitable manner. In the example, the rod can be biased closed using a compression spring (or other elastomeric element), and configured to transition between the first valve configuration 32 and the second valve configuration 33 upon user input (e.g., by pushing a button on the test container or the analysis device, by inputting a command at a user interface, etc.) and/or automatically (e.g., controlled by a controller of the system 100).

In another example, the outlet port 136 can include a material valve 138 configured to transition from a first state 34 to a second state 35 (e.g., reversibly, irreversibly), thereby allowing a volume of the dispersion to pass through the outlet port 136 in a controlled manner. In variations of this example, the material of the valve 138 can include any one or more of: a material (e.g., salt, sugar, polyvinyl alcohol, etc.) configured to transition from a solid state to a dissolved state (e.g., in a manner that does not affect detection of an analyte at the detection substrate), a wax configured to transition from a solid state to a melted state, and any other material configured to transition between states without affecting test results.

In another example, the outlet port 136 can be appropriately dimensioned (e.g., based upon the viscosity of the dispersion) to allow the controlled volume of the dispersion to pass into the analysis chamber 140. In variations of this example, positive pressure and/or negative pressure can also be used to drive the dispersion out of the port and into the analysis chamber.

In still another example, the outlet port 136 can include a valve 138 (e.g., a membrane, a film) that can be punctured or otherwise compromised to allow a volume of the dispersion to pass through the outlet port 136 and into the analysis chamber 140. In this example, the valve 138 could be compromised using a needle coupled to a portion of the second chamber, wherein the needle could be deflected (e.g., by a portion of the analysis device 205, in combination with spring-loading of the needle) in a manner that prevents accidental deflection by a user or other entity in contact with the test container 105. As such, the actuation system 137 can operate as a release mechanism that allows the dispersion to be conducted to a detection substrate at the analysis chamber 140. The outlet port 136 and/or actuation system 137 can, however, be configured in any other suitable manner and/or comprise any other suitable elements that enhance detection at a detection substrate. For instance, one variation of the outlet port 136 can include a filter proximal the port that prevents material (e.g., material that could adversely affect detection) from passing into the analysis chamber 140 and/or from reaching the detection substrate 150.

Figure 7:
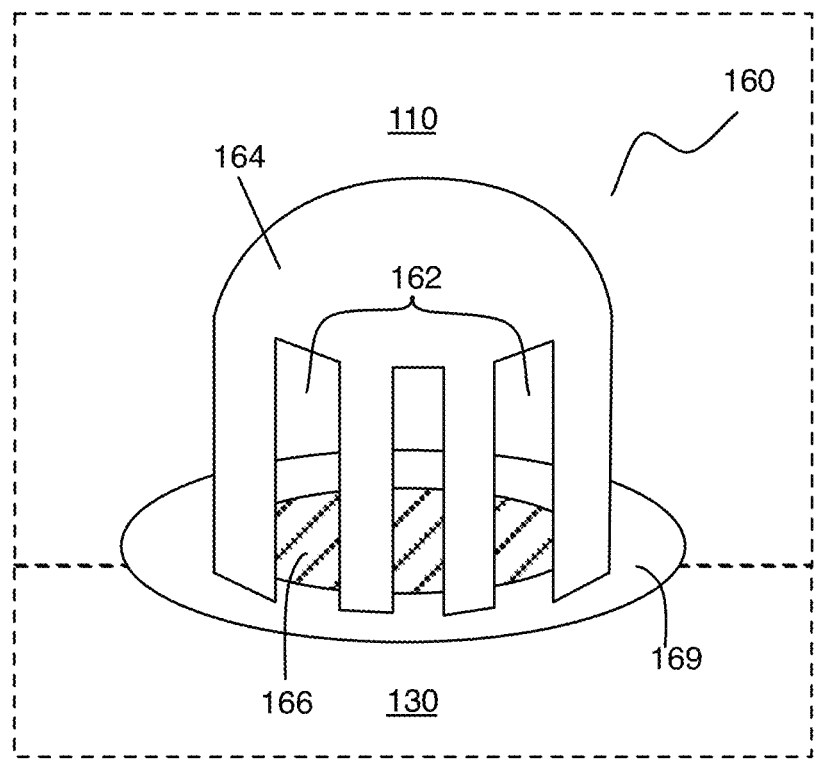
FIGS. 7 and 8 depict variations and configurations of a portion of a system for detection of harmful substances.
Figure 8:
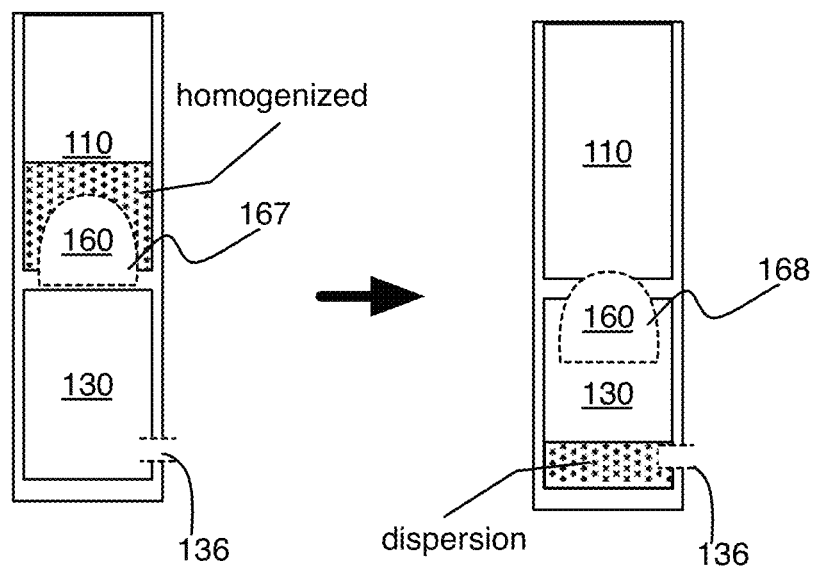

In some embodiments, as shown in FIGS. 2A, 2B, and 7, the system 100 can include a diaphragm 160 situated between the first chamber 110 and the second chamber 130, which functions to facilitate delivery of the homogenized sample, after processing of the consumable sample, into the second chamber 130 in a controlled manner. In one variation, the diaphragm 160 can include a set of openings 162 configured to allow passage of homogenized portions of the consumable sample, during processing, into a cavity formed by the diaphragm. In this variation, the diaphragm can further include a roof 164 at a superior portion of the diaphragm 160, wherein the roof 164 prevents passage of unprocessed portions of the consumable sample into the second chamber 130. In examples of this variation, the diaphragm has a height between 3 and 15 mm (e.g., 8 mm), in order to facilitate processing and transmission of a desired volume of the homogenized sample.

The set of openings 162 of the diaphragm 160 is preferably distributed uniformly about the second opening 114 of the first chamber 110 and/or the sample reception opening 132 of the second chamber 130, in order to facilitate reception of homogenized portions of the consumable sample into the diaphragm 160. However, the set of openings 162 can alternatively be arranged in any other suitable manner. The set of openings can be located at lateral surfaces (e.g., vertical surfaces) of the diaphragm 160, in the orientation of the diaphragm 160 shown in FIG. 7, and can additionally or alternatively be located at any other suitable surface of the diaphragm 160. Openings of the set of openings 162 are preferably rectangular in shape; however, the set of openings 162 can alternatively include openings that are any one or more of: polygonal, ellipsoidal, circular, and any other suitable shape. In variations, the set of openings 162 comprise rectangular openings that are from 2 mm to 15 mm in height (e.g., 7 mm in height) and 0.5 to 5 mm in width (e.g., 3 mm in width); however, other variations of the set of openings 164 can alternatively have any other suitable dimensions. Furthermore, the set of openings 162 can comprise non-identical openings (e.g., in shape, in dimensions, etc.) in other variations of the diaphragm 160.

The roof 164 of the diaphragm 160 is preferably non-planar (e.g., non-horizontally planar, in the orientation shown in FIGS. 2A and 7), and defines a concave surface facing the sample reception opening 132 of the second chamber 130, which promotes sliding of homogenized portions of the consumable sample off of the roof 164 and toward openings of the set of openings 162 of the diaphragm. The concave surface can be blunt or sharp, and in examples, can comprise a semi-spherical surface, a semi-conical surface, a semi-pyramidal surface, a prismatic surface, and/or any other suitable surface. Alternatively, the roof 164 of the diaphragm 160 can comprise a planar surface, or a non-concave surface.

The diaphragm 160 preferably has a first configuration 167 that retains at least a portion of the homogenized sample within the diaphragm 160 and a second configuration 168 that facilitates delivery of the homogenized sample into the sample reception opening 132 of the second chamber 130. In relation to the plunger 128 of the driving element 120 described above, the plunger 128 can be configured to be depressed or otherwise moved in any other suitable fashion in order to transition the diaphragm 160 between the first configuration 167 and the second configuration 168. In a first variation, the first configuration 167 is a raised configuration wherein a majority of the diaphragm 160 is situated within the first chamber 110, and openings of the diaphragm 160 are accessible from within the first chamber 110. In the first variation, the second configuration 167 is a depressed configuration wherein a majority of the diaphragm 160 is situated within the second chamber 130, and openings of the diaphragm 160 are substantially inaccessible from within the first chamber 110 (but open to the second chamber 130). In this variation, the diaphragm 160 can include at least one lip 169 circumscribing a portion of the diaphragm, wherein the lip 169 functions as a stop that constrains a range of motion of the diaphragm 160 between the first configuration 167 and/or the second configuration 168. Variations of the diaphragm 160 can, however, omit a lip 169. For instance, in variations wherein the diaphragm 160 can function as a mixing element 134, as described above, the diaphragm 160 can be configured to enter the second chamber 130 (e.g., drop entirely into the second chamber 130), and function as a mixing element that complements a mixing module of an analysis device 205. In a second variation, the first configuration 167 of the diaphragm 160 is an undeformed configuration, wherein a majority of the diaphragm 160 is situated within the first chamber 110, and openings of the diaphragm 160 are accessible from within the first chamber 110. In the second variation, the second configuration is a deformed configuration whereby at least one portion (e.g., the roof 164) of the diaphragm 160 is deformed to drive homogenized portions of the consumable sample from an interior portion of the diaphragm 160 and into the second chamber 130. In any of these variations, the diaphragm can be configured to be reversibly transitioned between the first configuration 167 and the second configuration 168; however, the diaphragm 160 can alternatively be configured to not be reversibly transitioned between the first configuration 167 and the second configuration 168.

The diaphragm 160 can additionally or alternatively include a temporary obstruction region 166, opposite the roof 164, that retains at least a portion of the homogenized sample within the diaphragm 160. Retention of the portion of the homogenized sample can be performed by the temporary obstruction region 166 in the first configuration 168 of the diaphragm 160, and/or in any other suitable configuration of the diaphragm 160. In one example, the temporary obstruction region 166 can comprise a dissolvable membrane configured to dissolve and release the homogenized sample into the second chamber 130 after a desired condition (e.g., a condition involving a threshold volume of the homogenized sample within the diaphragm) has been met. In another example, the temporary obstruction region 166 can comprise a screen (e.g., a mesh screen, a filter) configured to further facilitate processing of the consumable sample/homogenized sample to have a desired particle dimension prior to transmission into the second chamber 130. The temporary obstruction region 166 can, however, comprise any other suitable materials and/or be configured in any other suitable manner.

While a first chamber 110 and a second chamber 130 are described above, in some variations, the test container 105 can comprise a single chamber configured to perform the functions of the first chamber 110 and the second chamber 130. For instance, in one variation, the first chamber 110 and the second chamber 130 can be physically contiguous as a single chamber can be used to receive a consumable sample, and to facilitate grinding and mixing of the consumable sample with one or more process reagents to extract and/or dilute a test sample for delivery to a detection substrate 150 for analysis. As such, the first chamber 110 and the second chamber 130 can be distinct from each other, or otherwise integrated into a single chamber that facilitates all sample processing performed using the system 100.

The analysis chamber 140 functions to position a detection substrate 150 proximal the outlet port 136 of the second chamber, such that the detection substrate 150 can absorb a volume of the dispersion and provide indication of presence of at least one harmful substance within the consumable sample. The analysis chamber 140 is preferably coupled to at least one of the second chamber 130 and the first chamber, and in one variation, the analysis chamber 140 is configured external to the second chamber 130, with access between the second chamber 130 and the analysis chamber 140 provided by the outlet port 136 of the second chamber 130. In an example of this variation, the analysis chamber 140 can comprise a slot longitudinally spanning a portion of the test container 105, as shown in FIG. 2B, wherein the slot is configured to position the detection substrate 150 proximal the outlet port 136. However, the analysis chamber 140 can alternatively be configured in any other suitable manner.

The detection substrate 150 functions to indicate presence of an analyte, associated with a harmful substance, and in variations, can indicate presence based upon one or more of: a color change, fluorescence emission, infrared emission, magnetic response, electrical response, acoustic change, and any other suitable mechanism of indication. The detection substrate 150 is preferably a permeable substrate (e.g., test strip) that soaks up a portion of the dispersion and facilitates binding of one or more analytes in the dispersion with complementary antibodies (e.g., antibodies bound to cellulose nanobeads) at the detection substrate 150, to provide indication of presence of harmful substances associated with the analyte(s). The detection substrate 150 can include a single active region (e.g., a band, a line, a dot, etc.) for analyte binding, or a set of active regions for analyte binding. The active region(s) can include antibody cocktails for a single analyte associated with a harmful substance, a set of analytes associated with different harmful substances, and/or a control region configured provide a control readout (e.g., in order to enable determination of a baseline signal, in order to establish proper conductance of a test). For instance, in some variations of a detection substrate 150 with a set of active regions 151 for analyte binding, one active region can be used as a test region that is used to indicate an amount (e.g., concentration, volume, mass) of a harmful substance in a consumable sample, and another active region can be used as a control region that indicates that the test has been performed properly (i.e., such that data generated from the detection substrate 150 is reliable).

In variations, a region of a detection substrate 150 can be configured to accommodate an analyte with a single binding site, or multiple binding sites (e.g., as in a sandwich assay having a first antibody that serves as a capture antibody, and a second antibody that serves as an analyte-specific antibody). However, the detection substrate 150 can additionally or alternatively comprise any other suitable liquid medium or sensor configured to indicate presence of a harmful substance within the consumable sample in any other suitable manner. In an example, the detection substrate 150 is a long, narrow, and flat strip of a fibrous material with regions (e.g., bands, lines, spots) of complementary antibodies to an analyte associated with a harmful substance, whereby capillary soaking of the detection substrate 150 distributes the dispersion across the detection substrate 150. In a version of the example for gluten testing, the detection substrate 150 includes a control band and a test band, having a distribution of a G12 antibody, bound to cellulose nanobeads, which is configured to bind to the 33-mer peptide of the alpha-gliadin molecule in gluten.

In some variations, the analysis chamber 140 can include a detection window 142 that enables detection of presence of a harmful substance at the detection substrate 150. As such, the detection substrate 150 can be configured to align with the detection window, such that indicators (e.g., one or more lines generated during binding of analyte at the detection substrate) can be observed through the detection window 142. The detection window 142 can substantially span an entirety of the detection substrate, or can alternatively be configured to provide observation of one or more regions of interest of a detection substrate 150. Furthermore, the detection window 142 can comprise an opening through the analysis chamber 140, and can additionally or alternatively include a covering (e.g., transparent covering, translucent covering) that enables observation of the detection substrate 150. In variations, the detection window 142 can further function to indicate potential defectiveness of a test container 105, detection substrate 150, and/or any other suitable portion of the system 100 in providing reliable results. For instance, in some variations, wherein detection substrates are sensitive to heat and/or humidity, the detection window 142 can be configured to indicate subjection of a detection substrate 150 to high temperatures (e.g., above 40° C.) and/or humid environments (e.g., by producing a color change in the detection window, by having the detection window fog up, etc.). Additionally or alternatively, the test container 105 can be coupled with a dessicant to prevent humidity-induced damage, and furthermore, variations of the detection window 142 can additionally or alternatively provide any other suitable function that provides information regarding potential defectiveness of a test performed using the detection substrate 150, defectiveness in analyte detection, and/or any other suitable function. For instance, the detection window 142 can provide optical qualities that provide desired properties upon illumination in order to enhance analysis of a detection substrate 150. Variations of the analysis chamber 140 can, however, entirely omit the detection window 142. For instance, a variation of the system 100 can be configured such that the detection substrate is retrieved after contacting a volume of the dispersion, and analyzed away from an analysis chamber 140 of a test container 105.

Variations of the test container 105, as noted earlier, can be characterized by modularity in using a combination of reusable and/or non-reusable components, such that portions of the test container 105 can be reused, and other portions of the test container 105 can be disposed after a limited number of uses. For instance, in some variations, all portions of the test container 105 can be configured to be reusable, aside from the detection substrate 150/analysis chamber 140, such that the detection substrate 150 are disposed after each use, and the test container 105 can be reused for another instance of detection upon replacement of the detection substrate 150/analysis chamber. In other variations, all portions of the test container 105 can be configured to be reusable, aside from the detection substrate 150, such that the detection substrate 150 are disposed after each use, and the test container 105 can be reused for another instance of detection upon replacement of the detection substrate 150. The test container 105 can, however, provide any other suitable combination of reusable and disposable components. In providing modularity, portions of the test container 105 are preferably composed of a material that is recyclable and/or processable, and in variations, can comprise any one or more of: a polymer (e.g., a plastic), a metal, and a glass. However, variations of the test container 105 can alternatively comprise any other suitable material (e.g., ceramic), and can be configured to be entirely reusable or entirely disposable.

As a person skilled in the art will recognize from the previous detailed description and from the figures and claims, modifications and changes can be made to the embodiments of the test container 105 without departing from the scope of the test container 105.

1.2 System—Analysis Device

As noted above and shown in FIG. 1, in an embodiment, the analysis device 205 includes: a receiving port 210 configured to receive the test container 105, a mixing module 230 configured to mix the homogenized sample with a process reagent, an optical sensing subsystem 220 configured to enable detection of presence of the harmful substance at the detection substrate 150, and a processing and control system 240 configured to receive and process signals from the optical sensing subsystem 220, thereby producing an output indicative of presence of the harmful substance in the consumable sample.

The receiving port 210 functions to receive the test container 105, and can additionally function to align the test container 105 to facilitate detection of analytes at a detection substrate, in cooperation with the optical sensing subsystem 220. As such, the receiving port 210 preferably mates with the test container 105 (e.g., an external morphology of the test container 105), in a consistent manner, such that the test container 105 can only be positioned within the receiving port 210 of the analysis device in one of a discrete set of orientations (e.g., in variations wherein the test container 105 has an orientation). Alternatively, in variations wherein the test container 105 is symmetric (e.g., having a rotational axis of symmetry), the receiving port 210 can be configured to accommodate symmetry in the test container 105 in relation to positioning the test container 105 relative to other elements of the analysis device 205 (e.g., the optical sensing subsystem 220, the mixing module, 230). While the receiving port 210 can receive a test container 105 into an interior portion of the analysis device 205, receiving port 210 can additionally or alternatively be configured to couple the test container 105 to an external portion of the analysis device 205. For instance, the receiving port 210 can include a mechanism (e.g., latch, slide, magnet) configured to couple the test container 105 to at least a portion of the exterior of the analysis device 205.

Figure 9A:
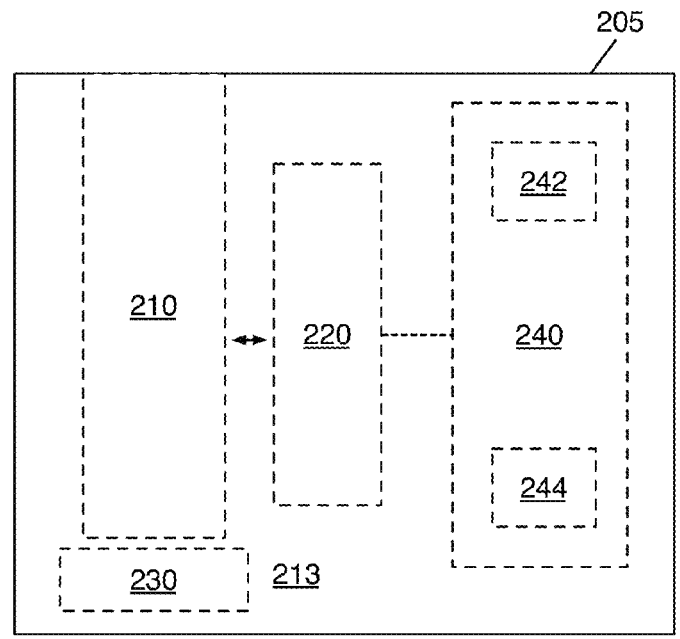
FIGS. 9A-9E depict variations and configurations of a portion of a system for detection of harmful substances.
Figures 9B, 9C:
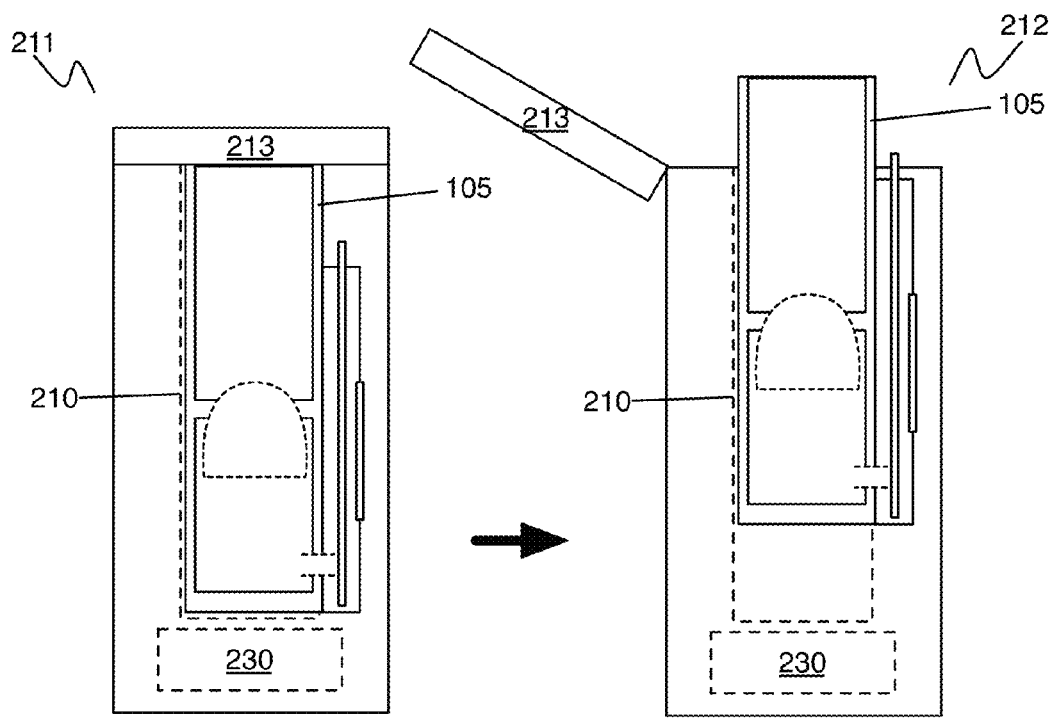
Figures 9D, 9E:
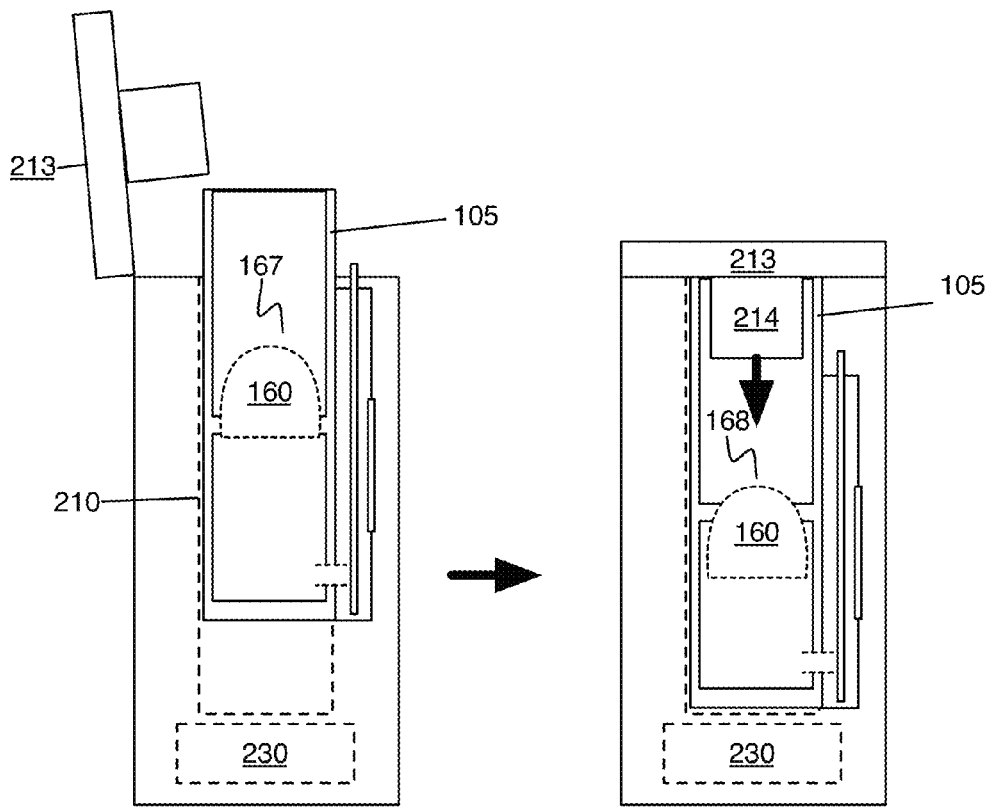

As such, in some variations, the receiving port 210 is preferably configured to receive the test container 105 in an alignment configuration 211, and to release the test container 105 from the analysis device 205 in a releasing configuration 212 (e.g., post-analysis of a sample), as shown in FIGS. 9A-9C. In producing the alignment configuration 211, the receiving port 210 can be coupled to a cap 213 or other mechanism (e.g., latch, tab, etc.) that facilitates retention (e.g., locking) of the test container 105 in the alignment configuration, thereby preventing undesired deviations from the alignment configuration, which could affect analysis of a detection substrate 150 of the test container 105. In variations of the receiving port 210 with a cap 213, the cap 213 can further function to facilitate processing of a consumable sample and/or homogenized sample within the test container. For instance, in one variation, the cap 213 can include an actuating element 214 (e.g., disposed within an interior surface of the cap 213, accessible from an exterior surface of the cap 213, etc.) configured to depress a plunger 128 of the test container 105 to transition a diaphragm between the first chamber 110 and the second chamber 130 of the test container 105 between a first configuration 167 and a second configuration 168, as shown in FIGS. 9D and 9E. The actuating element 214 can be magnetically driven, pneumatically driven, mechanically driven (e.g., using springs, etc.), or driven in any other suitable manner. Actuation of a plunger 128, as facilitated by the cap 213, in this variation can be automatically performed once the test container 105 is in the alignment configuration within the receiving port 210, and/or can be triggered (e.g., by the user, by a control system of the analysis device 205) in any other suitable manner. As such, in an example workflow of this variation, a user can place a test container 105 within the receiving port 210 of the analysis device, with the consumable sample substantially homogenized and the diaphragm 160 in the first configuration 167, and closing of the cap 213 can automatically initiate depressing of the plunger 128 to transition the diaphragm 160 into the second configuration 168 (e.g., without knowledge by the user). Then, after detection using the optical sensing subsystem 220, as described below, the cap 213 can be opened and the test container 105 can be released from the analysis device 205 in the releasing configuration. However, variations of the receiving port 210 can alternatively omit a cap or other mechanism configured to retain the test container 105 in the alignment configuration.

The mixing module 230 functions to facilitate active mixing of a homogenized sample of the test container 105 with a process reagent (e.g., extraction reagent), in order to produce a dispersion that can be delivered to a detection substrate for analysis. The mixing module 230 preferably operates in cooperation with a mixing element 134 of the test container 105 (e.g., of a second chamber 130 of the test container), thereby forming a complementary portion of a mechanism that provides solution mixing. Thus, the mixing module 230 is preferably situated proximal to a portion of the test container 105 having the homogenized sample and the process reagent, in the alignment configuration of the test container 105. As noted above and shown in FIG. 5, the mixing module 230 can provide a magnetically-driven mechanism of mixing, an ultrasonic mechanism of mixing, a vibration-based mechanism of mixing (e.g., mechanically driven, acoustically driven), a rocking motion, a spinning-based mechanism of mixing (e.g., by forming a vortex), a shaking-based mechanism of mixing, and any other suitable mechanism of mixing. In an example wherein the second chamber 130 of a test container 105 includes a magnetic mixing element 134, the mixing module 230 can comprise a complementary magnet situated proximal to the second chamber 130 in the alignment configuration of the system 100. In the example, the complementary magnet of the mixing module can be coupled to a spinning motor, thereby producing rotation at the magnetic mixing element 134 within the second chamber 130. In variations of this example, the mixing module 230 can be configured to detect proper coupling between the complementary magnet of the mixing module 230 and the magnetic mixing element 134 within the second chamber 130 of the test container 105 (e.g., by way of sensing of a magnetic force, by way of detection of motion of the magnetic mixing element 134 in response to motion of the complementary magnet, etc.). The mixing module 230 can, however, be configured in any other suitable manner.

Figure 10:
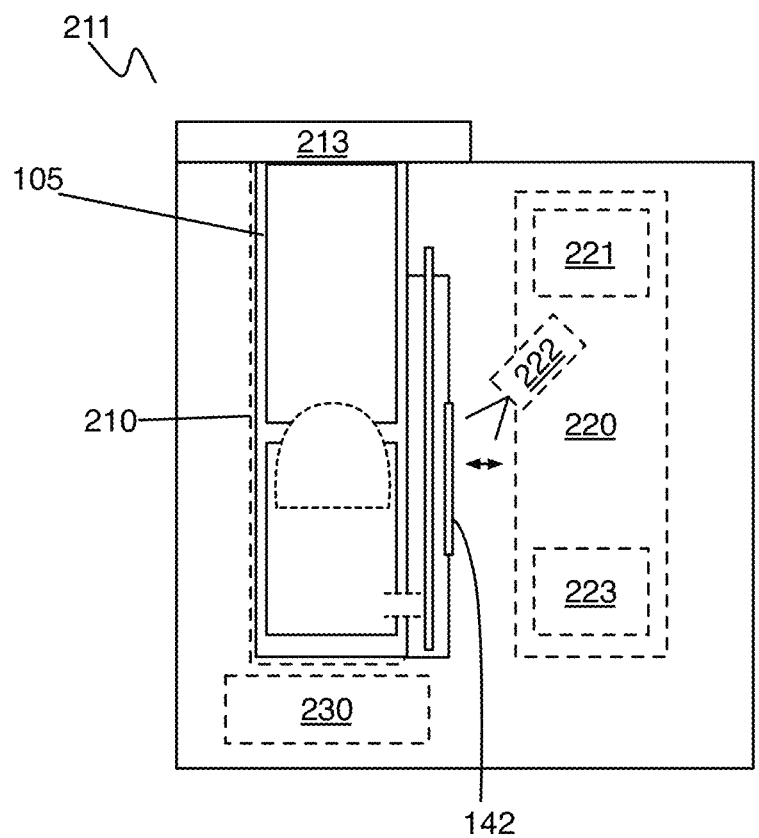
FIG. 10 depicts one variation of a portion of a system for detection of harmful substances.

The optical sensing subsystem 220 functions to facilitate detection of one or more analytes, indicative of presence of a harmful substance within a consumable sample. The optical sensing subsystem 220 further functions to facilitate automated reading of a detection substrate 150, such that effects of user error are minimized; however, the optical sensing subsystem 220 can be configured to provide manual assessment of test results of a detection substrate 150. The optical sensing subsystem 220 is preferably aligned with the detection window 142 of the analysis chamber 140 of the test container 105 in the alignment configuration 211, as shown in FIG. 10, in order to provide a compact configuration and facilitate direct communication between a detection substrate and the optical sensing subsystem 220. However, in other variations, the detection window 142 of the analysis chamber 140 and the optical sensing subsystem 220 can alternatively be misaligned, and configured to communicate using elements (e.g., mirrors, etc.) that facilitate indirect communication between a detection substrate 150 and the optical sensing subsystem 220. The optical sensing subsystem 220 preferably has an adequate sensitivity, resolution, and window of view in order to accurately and reliably detect signals from a detection substrate 150. In one variation, the sensitivity, resolution, and window of view cooperate to enable detection of a single analyte at a single region (e.g., dot, line, band) of a detection substrate 150 and in another variation, the sensitivity, resolution, and window of view cooperate to enable detection of multiple analytes (e.g., associated with different allergens) and/or control signals at multiple regions (e.g., dots, lines, bands) of a detection substrate 150. While one optical sensing subsystem 220 is described, the analysis device 205 can, however, include any other suitable number of optical sensors 220 to facilitate detection of one or more analytes at one or more regions of a detection substrate 150.

In a first variation, the optical sensing subsystem 220 can comprise a camera module 221 that is configured to image a detection substrate 150, through the detection window 142, and to generate a distribution (e.g., array) of pixel intensities corresponding to regions of the detection substrate. Then, in communication with the processing and control system 240

Figure 11A:
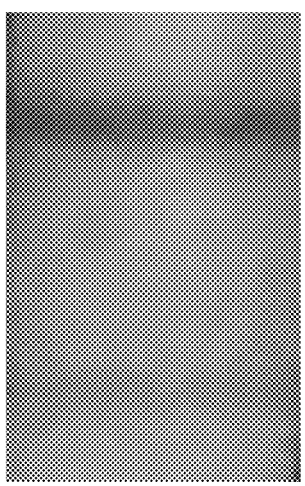
FIGS. 11A and 11B depict example outputs of a system for detection of harmful substances.
Figure 11B:
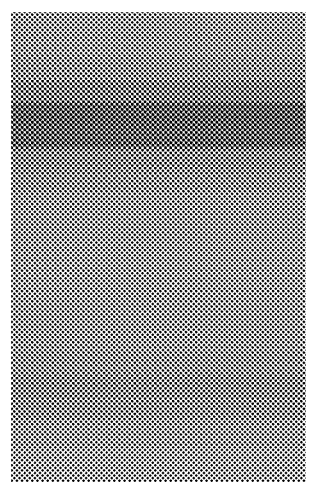

(described in further detail below), the distribution of pixel intensities generated from processing of a detection substrate 150 can be used to output a value of a parameter associated with an amount (e.g., concentration in parts per million, other concentration, mass, volume, etc.) of a harmful substance present in a consumable sample analyzed using the detection substrate 150. An example of pixel intensity distributions, prior to and post processing at the processing and control system 240, is shown in FIGS. 11A and 11B, respectively. The camera module 221 of the first variation preferably provides data within sufficient resolution to eliminate a requirement for tight coupling between the camera module 221 and a detection substrate 150; however, the camera module 221 can alternatively provide data with any other suitable resolution.

In the first variation, the camera module 221 can be provided along with an illumination module 222 configured to facilitate illumination of the detection substrate 150, in order to enable detection of the analyte(s) at the detection substrate. Illumination is preferably provided at an angle (e.g., an acute angle of incidence) relative to a surface of the detection window 142, in order to minimize reflection (e.g., from the detection window 142) that could interfere with sensing by the optical sensing subsystem 220. In specific examples, the illumination module can include one or more light-emitting diodes (LEDs) any/or any other suitable light sources. The LEDs/light sources can be configured to provide white light, or any suitable range of wavelengths of light. Furthermore, in variations wherein the illumination module 222 includes multiple light sources, the light sources can be identical in output (e.g., intensity, wavelength) or non-identical in output. As such, illumination can allow an intensity of a desired signal (e.g., indicative of an analyte associated with a harmful substance) to be enhanced. Illumination can additionally or alternatively function to remove signal interference due to inherent features (e.g., color, acidity, consistency, fermentation, hydrolyzation, etc.) of a consumable sample. For instance, pigmented and/or acidic foods can provide signal interference in a color-based assay. As such, illumination and or detection at an optical sensing subsystem 220 of the camera module 221 can be enabled in cooperation with one or more filters (e.g., wavelength filters, emission filters, excitation filters, etc.) configured to filter out any interfering signals.

Figure 12:
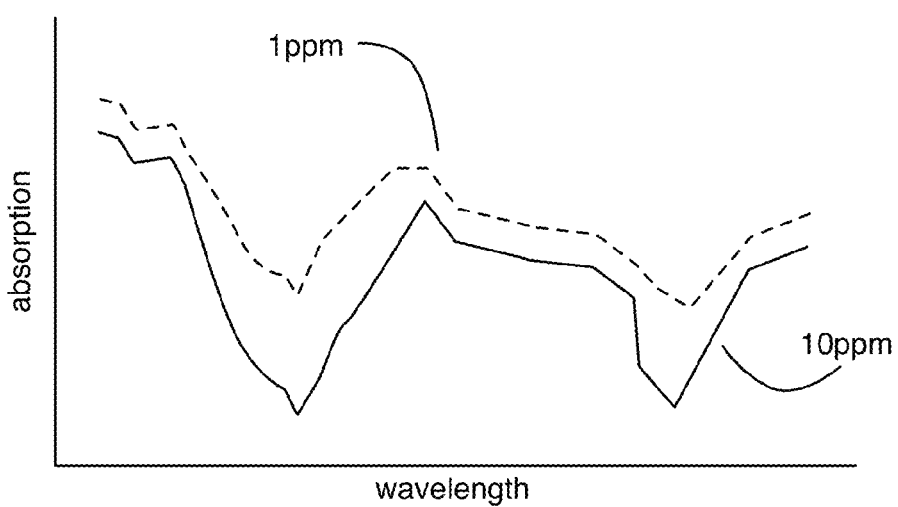
FIG. 12 depicts an example output of a system for detection of harmful substances.

In a second variation, the optical sensing subsystem 220 can comprise a photodiode system 223 that is configured to detect absorption and/or emission of light (e.g., wavelengths of light) indicative of presence of (i.e., an amount of) an analyte at a detection substrate in communication with the photodiode system 223. In one variation, the photodiode system 223 can include a photodiode configured to detect absorption of light associated with a peak absorption wavelength of an active region of a detection substrate (e.g., in order to assess absorption at a characteristic peak absorption wavelength of an antibody-coated bead bound to an analyte associated with a harmful substance). In one example for gluten detection, the photodiode system 223 can include a photodiode configured to detect absorption of 555 nm light at a detection substrate, wherein cellulose nanobeads treated with a complementary antibody for gluten have an absorption peak at 555 nm. In this example, a higher degree of absorption of 555 nm light (e.g., as indicated by a lower photodiode output) within an active region of a detection substrate 150 is associated with a higher concentration of gluten in a consumable sample, with an example of output data shown in FIG. 12.

In the second variation, the photodiode system 223 can be provided along with an illumination module 222 configured to facilitate illumination of the detection substrate 150, in order to enable detection of the analyte(s) at the detection substrate. Illumination is preferably provided at an angle (e.g., an acute angle of incidence) relative to a surface of the detection window 142, in order to minimize reflection (e.g., from the detection window 142) that could interfere with sensing by the optical sensing subsystem 220. In specific examples, the illumination module can include one or more light-emitting diodes (LEDs) and/or any other suitable light sources. The LEDs/light sources can be configured to provide light associated with an absorption peak of active particles (e.g., antibody-coated nanobeads, colloidal gold particles) at an active region of a detection substrate 150, or any suitable range of wavelengths of light. These particles can be either chemically conjugated with an antibody or more than one antibody, or can have the antibody or antibodies physically adsorbed onto them. Furthermore, in variations wherein the illumination module 222 includes multiple light sources, the light sources can be identical in output (e.g., intensity, wavelength) or non-identical in output. As such, illumination can allow an intensity of a desired signal (e.g., indicative of an analyte associated with a harmful substance) to be enhanced. Illumination can additionally or alternatively function to remove signal interference due to inherent features (e.g., color, acidity, consistency, fermentation, hydrolyzation, etc.) of a consumable sample. For instance, pigmented and/or acidic foods can provide signal interference in a color-based assay. The signal transduction mechanism can be based on any one or more of: absorption, fluorescence, chemiluminescence, Förster resonance energy transfer, electrical transduction, and any other suitable signal transduction mechanism. As such, illumination and or detection at an optical sensing subsystem 220 of the camera module 221 can be enabled in cooperation with one or more filters (e.g., wavelength filters, emission filters, excitation filters, etc.) configured to filter out any interfering signals.

The above variations of the optical sensor can be used in combination and/or provided by the system 100 in any suitable manner. Furthermore, in variations of a detection substrate 150 having multiple active regions, the optical sensor(s) 220 and/or illumination module(s) 222 can be provided in units, wherein the number of units is associated with a number of active regions in a detection substrate. For instance, for a detection substrate 150 having a control region and a test region, the system 100 can include two units, each having a photodiode and a light source (e.g., a 555 nm light source) configured to target each of the two active regions. In variations, however, the optical sensing subsystem 220 can be supplemented with or replaced with any other suitable sensor(s) configured to detect presence of an analyte based upon one or more of: color change, spectral emission, magnetic signals, electrical current, electrical bias, acoustic signals, and any other suitable mechanism.

The processing and control system 240 functions to receive signals from the optical sensor 240 and to generate an output indicative of presence of a harmful substance within the consumable sample, based upon signals generated from a detection substrate. The processing and control system 240 can further function to control operation of the analysis device 205, such that detection of one or more analytes associated with harmful substances in a consumable sample is, at least in part, automated. As such, the processing and control system 240 can include a processing module 242 configured to receive signals from the optical sensing subsystem 220 and a control module 244 configured to control operation of the analysis device.

The processing module 242 is preferably configured to condition signals generated at the optical sensor(s) 220, and can be directly coupled to an output of the optical sensor(s) 220. Alternatively, the processing module 242 can be configured to retrieve data generated from an output of an optical sensing subsystem 220 from a storage module or in any other suitable manner. The processing module 242 can thus be configured to perform any one or more of: denoising, filtering, smoothing, clipping, deconvolving, standardizing, detrending, resampling, and performing any other suitable signal-processing operation on output signals from the optical sensor(s) 220. In variations, wherein an output of the optical sensing subsystem 220 is image data, the processing module 242 can be configured to filter and/or condition image data for sharpness, saturation, edge-finding, intensity, and/or any other suitable image enhancement. The processing module 242 can further be configured to generate an analysis indicative of presence of the harmful substance, wherein the analysis provides information regarding an amount (e.g., concentration, volume, mass) of the harmful substance within the consumable sample. In one variation involving data from a photodiode, the analysis can enable identification of absorption peaks detected upon illumination of a detection substrate 150 (e.g., over time, taking into account kinetics of a reaction at the detection substrate), and associate an amount of absorption with an amount (e.g., concentration in parts per million) of an allergen present in the consumable sample. In one variation involving image data from a camera module, the analysis can characterize intensity (e.g., average intensity, peak intensity, relative intensity) across an active region of a detection substrate, and associate an intensity parameter (or other image parameter) with an amount (e.g., concentration in parts per million) of an allergen present in the consumable sample. The processing module 242 can be implemented in one or more processing elements (e.g., hardware processing element, cloud-based processing element), such that processing by the system 100 can be implemented in multiple locations and/or phases.

In variations, the control module 244 can be configured to control any one or more of: retaining a test container 105 within the analysis device 205 in an alignment configuration, facilitating release of the test container 105 from the analysis device 205 in the releasing configuration, depressing of a plunger 128 of the test container 105 (e.g., to transition a diaphragm 160 of the test container 105 between a first configuration and a second configuration), mixing of the homogenized sample with a process reagent upon transmission of commands to the mixing module 230, activation of a valve 138 of a second chamber 130 of the test container 105 in order to initiate delivery of a volume of a dispersion to a detection substrate 105, illumination of a detection substrate 150 upon transmission of commands to an illumination module 223, transmission of outputs of an optical sensor for conditioning an processing by the processing module 240, and any other suitable operation for automation in use of the system 100.

Modules of the processing and control system 240 can be implemented at any one or more of: on-board at the analysis device 205 that receives a test container 105, at a portion of the test container (e.g., using electronics integrated into the test container 105), and at any other suitable processing subsystem. For instance, modules of the processing and control module 240 can be implemented at a mobile device (e.g., smart phone, tablet, head-mounted computing device, wrist-mounted computing device) in communication with the analysis device 205, such that some amount of data processing and/or control of a test container 105 or analysis device 205 is implemented using the mobile device. Additionally or alternatively, modules of the processing and control system 240 can be implemented in any other hardware-based or cloud-based computing system configured to communicate with the system 100 described.

Furthermore, the analysis device 205 can include any other suitable elements configured to facilitate processing of a test sample (e.g., a dispersion generated from a consumable sample that has saturated a detection substrate), and/or reporting of information derived from the test sample to a user or other entity. In one variation, the analysis device 205 can include a module configured to facilitate release of the dispersion from the port 136 of the second chamber 130 to a detection substrate 150 at an analysis chamber 140, in cooperation with a valve 138 of the second chamber 130, as described in relation to the port 136 above. The analysis device 205 can further include elements that provide an indication that the analysis device is in an operational mode (e.g., as opposed to an off mode, as opposed to a dormant mode), and/or elements that reduce noise (i.e., signal noise, acoustic noise) during processing of a test sample. The analysis device 205 can further include a housing configured to house elements of the analysis device 205 in a compact manner. The analysis device 205 or any other suitable portion of the system 100 can further comprise a power module configured to provide power to the system 100 (e.g., by comprising an energy storing, energy receiving, and/or energy distributing element), a display (e.g., of the analysis device 205, of a mobile device in communication with the system 100) configured to convey information from the system 100 to a user or other entity, and/or any other suitable user interface elements (e.g., input modules, notification modules, etc.) configured to facilitate user interaction with the system 100. Additionally or alternatively, the analysis device 205 can include any other suitable elements for processing of a test sample in a manner that is convenient to a user.

As a person skilled in the art will recognize from the previous detailed description and from the figures and claims, modifications and changes can be made to the embodiments of the analysis device 205 without departing from the scope of the analysis device 205.

2. Method

Figure 13:
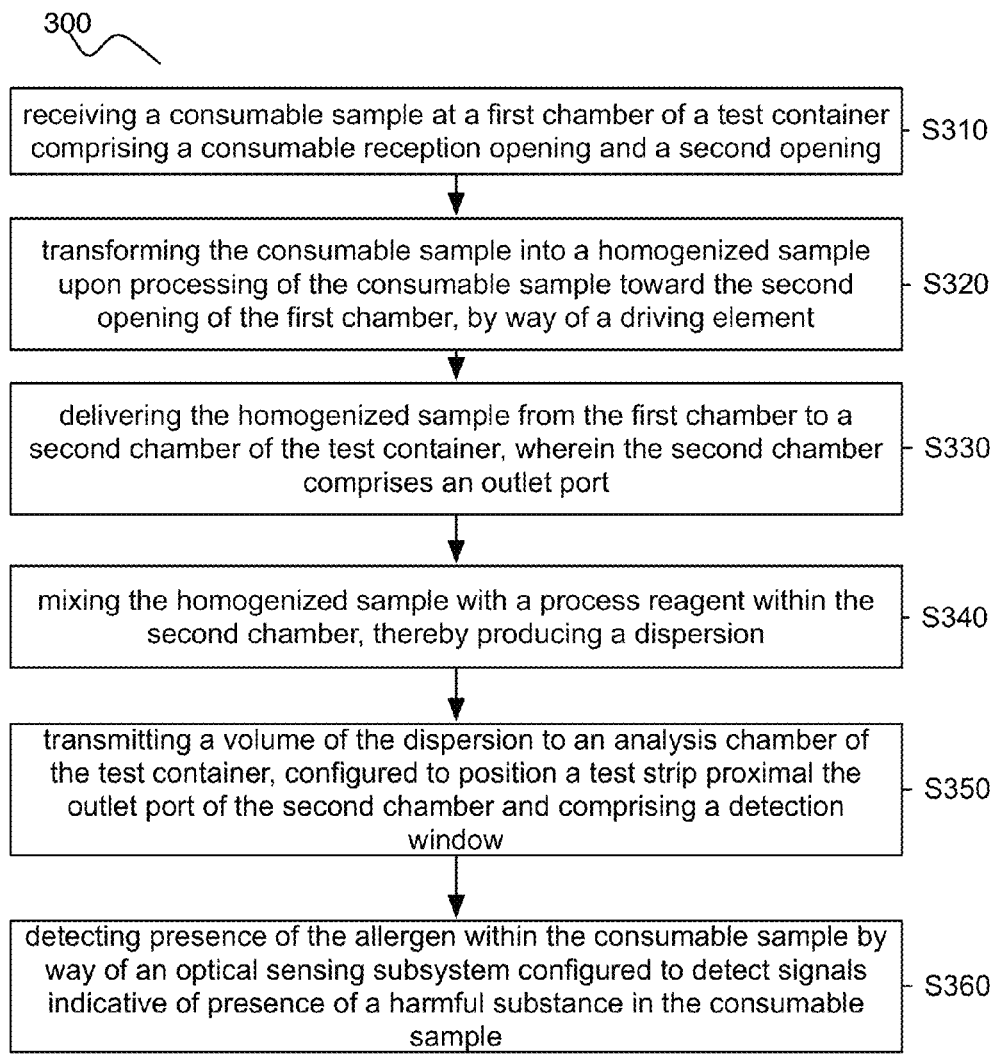
FIG. 13 depicts a flowchart schematic of an embodiment of a method for detection of harmful substances.
Figure 14:
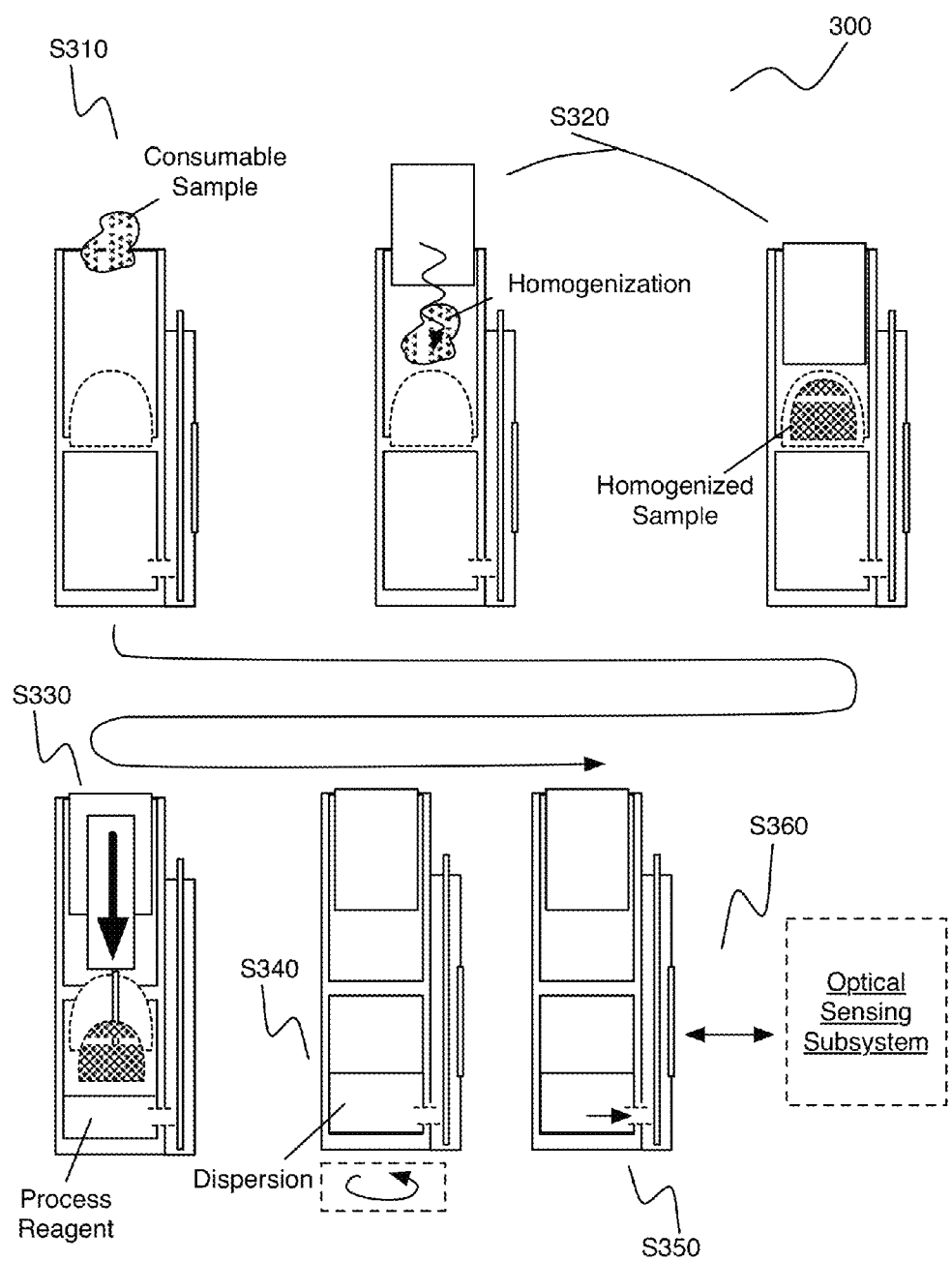
FIG. 14 depicts a schematic of an embodiment of a method for detection of harmful substances.

As shown in FIGS. 13 and 14, an embodiment of a method 300 for detecting a target substance in a consumable sample comprises: receiving a consumable sample at a first chamber of a test container comprising a consumable reception opening, configured to receive the consumable sample, and a second opening S310; transforming the consumable sample into a homogenized sample upon processing of the consumable sample toward the second opening of the first chamber by way of a driving element S320; delivering the homogenized sample from the first chamber to a second chamber of the test container, wherein the second chamber is configured to receive the homogenized sample from the second opening of the first chamber and comprises an outlet port S330; mixing the homogenized sample with a process reagent within the second chamber, thereby producing a dispersion S340; transmitting a volume of the dispersion to an analysis chamber, of the test container, configured to position a detection substrate proximal the outlet port of the second chamber and comprising a detection window that enables detection of presence of the allergen S350; and detecting presence of the harmful substance within the consumable sample by way of an optical sensing subsystem configured to detect signals indicative of the allergen through the detection window S360.

The method 300 functions to receive and process a sample of a consumable (e.g., food, beverage, cosmetic, etc.) in order to enable detection of one or more harmful substances within the sample. In examples, the harmful substances can include any one or more of: an allergen (e.g., gluten allergen, a dairy-derived allergen, a nut allergen, a fish allergen, an egg-derived allergen, etc.) a toxin, a bacterium, a fungus, a pesticide, a heavy metal, a chemical or biological compound (e.g., a fat, a protein, a sugar, a salt, etc.), and any other suitable harmful substance. The method 300 is preferably configured to impose minimal requirements upon a consumer using the system 100, in terms of labor-intensiveness, time-intensiveness, and cost-intensiveness. As such, the method 300 is preferably configured to automatically or semi-automatically process the sample in a manner that is intuitive to the consumer, and to quickly provide information regarding presence of the harmful substance(s) within the sample. The method 300 is preferably implemented at least in part by a portion of the system 100 described in Section 1 above; however, the method 300 can alternatively be implemented using any other suitable system.

Block S310 recites: receiving a consumable sample at a first chamber of a test container comprising a food reception opening, configured to receive the consumable sample, and a second opening. Block S310 functions to receive and facilitate processing (e.g., homogenization) of a consumable sample that the user intends to analyze for presence of a harmful substance. Block S310 is preferably implemented at an embodiment, variation, or example of the first chamber described in relation to the system 100 above; however, Block S310 can alternatively be implemented with any other suitable chamber configured to receive a solid and/or liquid sample. As such, Block S310 can comprise actively or passively receiving a consumable sample from the user. In variations of passive reception, the consumable sample can be tweezed, scooped, spooned, forked, or otherwise delivered into the first chamber in any other suitable manner. In variations of active reception, the consumable sample can be sucked or forced into the first chamber in any other suitable manner (e.g., using positive and/or negative pressure).

Block S320 recites: transforming the consumable sample into a homogenized sample upon processing of the consumable sample toward the second opening of the first chamber by way of a driving element. Block S320 functions to process the consumable sample to have particles of a desired size, and to increase homogeneity of a consumable sample received in Block S310, in order to generate reliable results regarding an amount (e.g., concentration, mass, volume) of a harmful substance within a consumable sample. Block S320 is preferably implemented using embodiments, variations, or examples of the first chamber, driving element 120, grinder 122, plunger 128, and/or diaphragm 160 of the test container 105 described in relation to the system 100 above; however, Block S320 can alternatively be implemented using any other suitable system. As such, in homogenizing the consumable sample, Block S320 preferably involves grinding the consumable sample with a set of protrusions of a driving element, using a combination of compression and rotational motions (e.g., involving threads of the first chamber and the driving element); however, Block S320 can additionally or alternatively produce the homogenized sample in any other suitable manner.

Block S330 recites: delivering the homogenized sample from the first chamber to a second chamber of the test container, wherein the second chamber is configured to receive the homogenized sample from the second opening of the first chamber and comprises an outlet port. Block S330 functions to deliver the homogenized sample for further processing in a controlled manner that ensures that homogenized portions of the consumable sample continue on for further processing, while un-homogenized portions of the consumable sample are either undelivered or are retained to be homogenized. Block S330 is preferably implemented using embodiments, variations, or examples of the first chamber, driving element 120, grinder 122, plunger 128, diaphragm 160, and/or second chamber 130 of the test container 105 described in relation to the system 100 above; however, Block S330 can alternatively be performed using any other suitable system 100. As such, Block S330 can include receiving homogenized portions of a consumable sample within a cavity of a diaphragm configured between the first chamber and the second chamber, and delivering homogenized portions of the consumable sample into the second chamber by depressing a plunger configured to contact the diaphragm. Block S330 can, however, include delivering the homogenized sample from the first chamber to a second chamber of the test container in any other suitable manner.

Block S340 recites: mixing the homogenized sample with a process reagent within the second chamber, thereby producing a mixture. Block S340 functions to facilitate extraction of analytes, associated with the harmful substance, from the homogenized sample, in order to facilitate detection of the analytes in subsequent blocks of the method 300. Block S340 is preferably implemented using embodiments, variations, or examples of the second chamber 130, the mixing element 134, and/or the mixing module 230 described in relation to the system 100 described above, however, Block S340 can alternatively be implemented using any other suitable system. As such, in variations, Block S340 can include providing a volume of the process reagent (e.g., prepackaged within the second chamber), such that the homogenized sample is automatically brought into contact with the process reagent upon delivery between the first chamber and the second chamber, as described in relation to Block S330. Additionally or alternatively, Block S340 can comprise actively delivering the process reagent to be mixed with the homogenized sample, by way of a fluid delivery module coupled to the first chamber and/or the second chamber. In Block S340, the process reagent preferably includes an extraction solution configured to extract at least one analyte, associated with a harmful substance, from the homogenized sample, that can be detected at a detection substrate and used to indicate presence of the harmful substance. However, the process reagent can additionally or alternatively include any other suitable reagents, as described above.

While blocks of the method 300 can occur as distinct steps, in some variations, portions of at least Blocks S310, S320, S330, and/or S340 can be performed substantially simultaneously. For instance, according to a variation of the method 300, a consumable sample can combined with a process reagent (e.g., an extraction solution, a dilution buffer, etc.) prior to or during grinding, thereby producing a mixture that can be delivered from a chamber of a test container and to a detection substrate for analysis.

Block S350 recites: transmitting a volume of the dispersion to an analysis chamber, of the test container, configured to position a detection substrate proximal the port of the second chamber and comprising a detection window that enables detection of presence of the allergen. Block S350 functions to control delivery of the dispersion to a detection substrate, such that an adequate volume of the dispersion is provided to a detection substrate to enable analyte detection, while avoiding flooding of the detection substrate. Block S350 is preferably implemented using embodiments, variations, or examples of the second chamber, outlet port, valve, and/or analysis chamber described in relation to the system 100 above; however, Block S350 can alternatively be implemented using any other suitable system. As such, Block S350 can comprise opening a valve (e.g., using a control module) of an outlet port of the second chamber, to deliver a volume of the dispersion to a detection substrate within the analysis chamber. However, Block S350 can comprise any other suitable step for delivery of a volume of the dispersion to the detection substrate.

Block S360 recites: detecting presence of the allergen or other substances within the consumable sample by way of an optical sensor configured to detect signals indicative of the allergen through the detection window. Block S360 functions to detect and process signals generated from a detection substrate treated with the dispersion, in order to generate an analysis that provides information regarding presence of one or more harmful substances within a consumable sample. Block S360 is preferably implemented using embodiments, variations, or examples of the analysis chamber, detection substrate, detection window, optical sensor, and/or processing and control system described in relation to the system 100 above; however, Block S360 can alternatively be performed using any other suitable system. As such Block S360 can include any one or more of: denoising, filtering, smoothing, clipping, deconvolving, standardizing, detrending, resampling, and performing any other suitable signal-processing operation on output signals from an optical sensor in communication with a detection substrate saturated with the dispersion. In variations of Block S360 involving image data, Block S360 can comprise filtering and/or conditioning image data for sharpness, saturation, edge-finding, intensity, and/or any other suitable image enhancement.

In generating an analysis in Block S360, the analysis preferably provides information regarding an amount (e.g., concentration, volume, mass) of the harmful substance within the consumable sample. In one variation involving data from a photodiode, generating the analysis in Block S360 can include identifying absorption peaks detected upon illumination of a detection substrate 150 (e.g., over time, taking into account kinetics of a reaction at the detection substrate), and associating an amount of absorption with an amount (e.g., concentration in parts per million) of an allergen present in the consumable sample. In one variation involving image data from a camera module, generating the analysis in Block S360 can comprise characterizing intensity (e.g., average intensity, peak intensity, relative intensity) across an active region of a detection substrate, and associating an intensity parameter (or other image parameter) with an amount (e.g., concentration in parts per million) of an allergen present in the consumable sample. Block S360 can, however, comprise processing signals derived from a detection substrate saturated with a volume of the dispersion, and/or generating an analysis in any other suitable manner.

The method 300 can additionally or alternatively include any other suitable blocks or steps configured to facilitate reception and/or processing of a consumable sample, in order to facilitate detection of the presence of one or more harmful substances within the consumable sample.

Embodiments of the system 100 and/or method 300 and variations thereof can be embodied and/or implemented at least in part by a machine configured to receive a computer-readable medium storing computer-readable instructions. The instructions are preferably executed by computer-executable components preferably integrated with the system 100 and one or more portions of the processor 273 and/or the controller 272. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system with a test container for detecting an allergen in a consumable sample, the test container comprising:
    a first chamber comprising a consumable reception opening, configured to receive the consumable sample, and a second opening;
    a driving element configured to interact with the first chamber and to generate a homogenized sample upon processing of the consumable sample toward the second opening of the first chamber;
    a second chamber comprising a sample reception opening, configured to receive the homogenized sample from the second opening of the first chamber, and an outlet port at a portion of the second chamber distal the first chamber;
    a diaphragm situated between the first chamber and the second chamber, the diaphragm having a first configuration that retains at least a portion of the homogenized sample within the diaphragm and precludes entry of the homogenized sample into the sample reception opening of the second chamber, and a second configuration that facilitates entry of the homogenized sample into the sample reception opening of the second chamber; and
    an analysis chamber configured to position a detection substrate proximal the outlet port of the second chamber and comprising a detection window that enables detection of presence of the allergen by way of inspection of the detection substrate through the detection window.

2. The system of claim 1, wherein the driving element includes a shaft and a set of protrusions proximal an end portion of the shaft, wherein the set of protrusions are configured to grind the consumable sample within the first chamber upon rotation of the shaft.

3. The system of claim 2, wherein the shaft is a threaded shaft configured to mate with threads at an internal surface of the first chamber, and wherein rotation of the threaded shaft drives and grinds the consumable sample during processing of the consumable sample from the consumable reception opening to the second opening.

4. The system of claim 1, wherein the diaphragm has a concave surface facing the sample reception opening of the second chamber, wherein a set of openings within the diaphragm, surrounding the sample reception opening, facilitate transmission of the homogenized sample from the first chamber into the second chamber.

5. The system of claim 4, wherein the diaphragm has a temporary obstruction region configured to retain at least a portion of the homogenized sample within the diaphragm in the first configuration, and wherein the temporary obstruction region comprises a dissolvable membrane configured to be bypassed upon accumulation of a desired volume of the homogenized sample within the diaphragm.

6. The system of claim 1, wherein the first configuration of the diaphragm is a raised configuration wherein a majority of the diaphragm is situated within the first chamber and openings of the diaphragm are accessible from within the first chamber.

7. The system of claim 6, wherein the driving element includes a grinder configured to rotate within the first chamber and having a concentric channel aligned with an axis of rotation of the grinder, and a plunger configured to pass through the grinder to contact the diaphragm.

8. The system of claim 7, wherein the second configuration of the diaphragm is a depressed configuration wherein a majority of the diaphragm is situated within the second chamber, and openings of the diaphragm are substantially inaccessible from within the first chamber 110 but open to the second chamber, and wherein the diaphragm is transitionable between the first configuration and the second configuration by passing the plunger through the grinder.

9. The system of claim 1, wherein the second chamber comprises a process reagent and a mixing element configured to actively facilitate mixing of the homogenized sample with the process reagent.

10. The system of claim 1, further including:
an analysis device comprising:
a receiving port configured to reversibly receive the test container in an alignment configuration and to deliver the test container from the analysis device in a releasing configuration; and
a mixing module configured to facilitate mixing of the homogenized sample within the second chamber of the test container in the alignment configuration.

11. The system of claim 10, wherein the mixing element of the second chamber of the test container is a first magnetic element, and wherein the mixing module comprises an actuator coupled to a second magnetic element configured to interact with the first magnetic element in the alignment configuration.

12. The system of claim 1, further including:
an analysis device comprising:
a receiving port configured to reversibly receive the test container in an alignment configuration and to deliver the test container from the analysis device in a releasing configuration; an
an optical sensor aligned with the detection window of the analysis chamber of the test container in the alignment configuration; and
a processing system configured to receive signals from the optical sensor and to generate an output indicative of presence of the allergen within the consumable sample.

13. The system of claim 12, wherein the detection substrate comprises at least one active region comprising antibody-treated particles, configured to bind to analytes associated with the allergen, thereby facilitating detection of presence of the allergen.

14. The system of claim 13, wherein the optical sensor comprises a camera module configured to detect image intensity, indicative of an amount of analytes associated with the allergen, at the detection substrate.

15. The system of claim 1, wherein the detection window of the analysis chamber is configured to provide indication of at least one of heat damage and humidity damage to the detection substrate.

16. The system of claim 1, wherein the first chamber and the second chamber are physically contiguous as a single chamber configured to receive the consumable sample, process the consumable sample to generate the homogenized sample, and to deliver a mixture derived from the homogenized sample to the detection substrate.

* * * * *